US009494577B2

(12) United States Patent
McGarr et al.

(10) Patent No.: US 9,494,577 B2
(45) Date of Patent: Nov. 15, 2016

(54) APPARATUS AND METHODS FOR THREE-DIMENSIONAL TISSUE MEASUREMENTS BASED ON CONTROLLED MEDIA FLOW

(71) Applicant: Seahorse Bioscience, Billerica, MA (US)

(72) Inventors: Paul McGarr, Longmeadow, MA (US); Andy C. Neilson, Sunapee, NH (US); Jay S. Teich, Berlin, MA (US)

(73) Assignee: Seahorse Biosciences, Billerica, MA (US)

( * ) Notice: Subject to any disclaimer, the term of this patent is extended or adjusted under 35 U.S.C. 154(b) by 128 days.

(21) Appl. No.: 14/079,022

(22) Filed: Nov. 13, 2013

(65) Prior Publication Data

US 2014/0170671 A1    Jun. 19, 2014

Related U.S. Application Data

(60) Provisional application No. 61/725,781, filed on Nov. 13, 2012.

(51) Int. Cl.
| | |
|---|---|
| *G01N 33/00* | (2006.01) |
| *G01N 33/50* | (2006.01) |
| *B01L 3/00* | (2006.01) |
| *C12M 1/32* | (2006.01) |
| *C12M 1/12* | (2006.01) |

(Continued)

(52) U.S. Cl.
CPC ......... *G01N 33/5091* (2013.01); *B01L 3/5025* (2013.01); *C12M 23/12* (2013.01); *C12M 25/04* (2013.01); *C12M 27/00* (2013.01); *C12M 29/10* (2013.01); *C12M 41/00* (2013.01); *C12M 41/32* (2013.01); *G01N 21/6452* (2013.01); *B01L 3/50853* (2013.01); *B01L 2200/026* (2013.01); *B01L 2300/046* (2013.01); *B01L 2300/0829* (2013.01); *B01L 2400/0478* (2013.01)

(58) Field of Classification Search
CPC ............ G01N 33/5091; G01N 21/6452; B01L 3/5025; B01L 3/50853
See application file for complete search history.

(56) References Cited

U.S. PATENT DOCUMENTS

| | | | |
|---|---|---|---|
| 4,016,617 A | 4/1977 | Cardus et al. | |
| 4,065,357 A | 12/1977 | Groves | |

(Continued)

FOREIGN PATENT DOCUMENTS

| | | |
|---|---|---|
| DE | 40 16 617 | 11/1991 |
| DE | 42 17 868 | 12/1993 |

(Continued)

OTHER PUBLICATIONS

Haber et al., "Flow Sensor Driven Nanodispensing: The Path to More Reliable Liquid Handling Operations", American Laboratory, Oct. 2004, pp. 32-36.

(Continued)

*Primary Examiner* — Melanie Y Brown

(57) ABSTRACT

An apparatus including a plurality of wells for conducting analysis of three-dimensional cell samples (e.g., tissue samples) and methods for experimenting with a three-dimensional sample. A removable insert for use with the apparatus enables plunger-driven perfusion of the three-dimensional sample.

25 Claims, 17 Drawing Sheets

(51) Int. Cl.
  *C12M 1/00* (2006.01)
  *C12M 1/34* (2006.01)
  *C12M 1/02* (2006.01)
  *G01N 21/64* (2006.01)

(56) References Cited

U.S. PATENT DOCUMENTS

| | | | |
|---|---|---|---|
| 4,217,868 A | 8/1980 | Grather et al. | |
| D258,145 S | 2/1981 | Potts | |
| 4,256,832 A | 3/1981 | Findl et al. | |
| D260,428 S | 8/1981 | Fekete | |
| D268,130 S | 3/1983 | Easton | |
| 4,405,375 A | 9/1983 | Gibson et al. | |
| 4,461,328 A | 7/1984 | Kenney | |
| 4,498,510 A | 2/1985 | Minshew, Jr. et al. | |
| D280,131 S | 8/1985 | Takasugi | |
| D280,663 S | 9/1985 | Albon et al. | |
| 4,599,315 A | 7/1986 | Terasaki et al. | |
| D285,118 S | 8/1986 | Huang | |
| 4,711,851 A | 12/1987 | McNamara et al. | |
| D300,245 S | 3/1989 | Navarro et al. | |
| D301,167 S | 5/1989 | Raybould et al. | |
| 4,879,097 A | 11/1989 | Whitehead et al. | |
| D324,426 S | 3/1992 | Fan et al. | |
| 5,104,804 A | 4/1992 | Humphries et al. | |
| 5,120,421 A | 6/1992 | Glass et al. | |
| D328,135 S | 7/1992 | Fan et al. | |
| D332,145 S | 12/1992 | Wada et al. | |
| 5,200,051 A | 4/1993 | Cozzette et al. | |
| D335,348 S | 5/1993 | Frenkel et al. | |
| D339,869 S | 9/1993 | Schea, III et al. | |
| 5,250,419 A | 10/1993 | Bernard et al. | |
| 5,264,103 A | 11/1993 | Yoshioka et al. | |
| 5,278,048 A | 1/1994 | Parce et al. | |
| 5,286,364 A | 2/1994 | Yacynych et al. | |
| 5,309,085 A | 5/1994 | Sohn | |
| 5,345,213 A | 9/1994 | Semancik et al. | |
| D351,661 S | 10/1994 | Fischer | |
| D359,125 S | 6/1995 | Livingston | |
| 5,459,300 A | 10/1995 | Kasman | |
| 5,466,348 A | 11/1995 | Holm-Kennedy | |
| 5,468,605 A | 11/1995 | Harris et al. | |
| 5,495,850 A | 3/1996 | Zuckerman | |
| 5,496,697 A | 3/1996 | Parce et al. | |
| 5,512,492 A | 4/1996 | Herron et al. | |
| 5,536,662 A | 7/1996 | Humphries et al. | |
| 5,567,598 A | 10/1996 | Stitt et al. | |
| 5,622,872 A | 4/1997 | Ribi | |
| 5,728,541 A | 3/1998 | Kornblith | |
| 5,766,875 A | 6/1998 | Hafeman et al. | |
| 5,774,214 A | 6/1998 | Prettyjohns | |
| 5,792,426 A | 8/1998 | Portmann et al. | |
| 5,830,138 A | 11/1998 | Wilson | |
| D404,497 S | 1/1999 | Lahm et al. | |
| D404,831 S | 1/1999 | Yamazaki et al. | |
| 5,959,297 A | 9/1999 | Weinberg et al. | |
| 5,998,517 A | 12/1999 | Gentle, Jr. et al. | |
| 6,030,917 A | 2/2000 | Weinberg et al. | |
| D421,498 S | 3/2000 | Livingston | |
| D423,679 S | 4/2000 | Jenkins et al. | |
| 6,078,698 A | 6/2000 | Lorton et al. | |
| 6,080,574 A | 6/2000 | Berndt | |
| D428,657 S | 7/2000 | Ward | |
| 6,083,761 A | 7/2000 | Kedar et al. | |
| 6,146,967 A | 11/2000 | Thakur et al. | |
| D438,631 S | 3/2001 | Miller | |
| D438,632 S | 3/2001 | Miller | |
| D438,633 S | 3/2001 | Miller | |
| 6,280,586 B1 | 8/2001 | Wolf et al. | |
| 6,306,658 B1 | 10/2001 | Turner et al. | |
| 6,376,233 B1 | 4/2002 | Wolf et al. | |
| 6,380,605 B1 | 4/2002 | Verhaegen | |
| 6,395,506 B1 | 5/2002 | Pitner et al. | |
| 6,395,555 B1 | 5/2002 | Wilson et al. | |
| 6,416,967 B2 | 7/2002 | Kornblith | |
| D461,554 S | 8/2002 | Lafond et al. | |
| 6,468,736 B2 | 10/2002 | Brooker | |
| D466,219 S | 11/2002 | Wynschenk et al. | |
| 6,486,947 B2 | 11/2002 | Modlin et al. | |
| D467,080 S | 12/2002 | Zimmerman | |
| 6,627,158 B1 | 9/2003 | Peltier | |
| 6,653,124 B1 | 11/2003 | Freeman | |
| 6,673,532 B2 | 1/2004 | Rao | |
| D486,580 S | 2/2004 | Abdel-Model | |
| D492,419 S | 6/2004 | Farina | |
| 6,766,817 B2 | 7/2004 | da Silva | |
| 6,821,787 B2 | 11/2004 | Neilson et al. | |
| 6,835,574 B2 | 12/2004 | Neilson et al. | |
| 6,880,158 B1 | 4/2005 | Basso et al. | |
| 6,881,584 B1 | 4/2005 | Lenhard et al. | |
| 6,887,680 B2 | 5/2005 | Kornblith | |
| 6,900,027 B1 | 5/2005 | Kornblith | |
| 6,918,404 B2 | 7/2005 | Dias da Silva | |
| 6,933,129 B1 | 8/2005 | Kornblith | |
| 7,066,586 B2 | 6/2006 | da Silva | |
| D529,184 S | 9/2006 | Bargh et al. | |
| 7,276,351 B2 | 10/2007 | Teich et al. | |
| D565,742 S | 4/2008 | Parunak et al. | |
| D566,291 S | 4/2008 | Parunak et al. | |
| 7,638,321 B2 | 12/2009 | Teich et al. | |
| D613,418 S | 4/2010 | Ryan et al. | |
| 7,704,475 B2 | 4/2010 | Bull et al. | |
| D617,468 S | 6/2010 | Marquordt et al. | |
| D618,821 S | 6/2010 | Larsen | |
| D619,257 S | 7/2010 | Meschenmoser et al. | |
| D624,661 S | 9/2010 | Himmelsbach et al. | |
| 7,795,012 B2 | 9/2010 | Lehmann et al. | |
| D628,305 S | 11/2010 | Gorrec et al. | |
| D628,306 S | 11/2010 | Blanc et al. | |
| 7,851,201 B2 | 12/2010 | Teich et al. | |
| D631,557 S | 1/2011 | Tajima et al. | |
| D632,402 S | 2/2011 | Sattler et al. | |
| D651,802 S | 1/2012 | Riedesel et al. | |
| D657,473 S | 4/2012 | Miyashita et al. | |
| 8,202,702 B2 | 6/2012 | Neilson et al. | |
| D669,594 S | 10/2012 | Cao et al. | |
| D672,053 S | 12/2012 | Chen et al. | |
| D673,293 S | 12/2012 | Demas et al. | |
| D674,112 S | 1/2013 | Demas et al. | |
| D686,311 S | 7/2013 | Mori | |
| D686,749 S | 7/2013 | Trump | |
| D694,904 S | 12/2013 | Banes et al. | |
| D694,906 S | 12/2013 | Priebe et al. | |
| D694,908 S | 12/2013 | Okihara | |
| D696,419 S | 12/2013 | Fusellier et al. | |
| 8,658,349 B2 | 2/2014 | Teich et al. | |
| D701,972 S | 4/2014 | Ohmae | |
| 8,697,431 B2 | 4/2014 | Teich et al. | |
| D707,847 S | 6/2014 | Motadel et al. | |
| D714,957 S | 10/2014 | Smith | |
| D717,470 S | 11/2014 | Demas et al. | |
| D720,468 S | 12/2014 | Calderwood et al. | |
| 2001/0039045 A1 | 11/2001 | Chan et al. | |
| 2001/0051353 A1 | 12/2001 | Kornblith | |
| 2002/0025547 A1 | 2/2002 | Rao | |
| 2002/0059945 A1* | 5/2002 | Maiefski | B01J 19/0046 134/25.1 |
| 2002/0098592 A1 | 7/2002 | Neilson et al. | |
| 2002/0098593 A1 | 7/2002 | Nelson et al. | |
| 2002/0132360 A1 | 9/2002 | Neilson et al. | |
| 2002/0146345 A1 | 10/2002 | Neilson et al. | |
| 2002/0146836 A1 | 10/2002 | Neilson et al. | |
| 2002/0168679 A1 | 11/2002 | Naus et al. | |
| 2002/0182720 A1 | 12/2002 | Gevaert et al. | |
| 2002/0192638 A1 | 12/2002 | Kornblith | |
| 2003/0059807 A1 | 3/2003 | Roach et al. | |
| 2003/0124029 A1* | 7/2003 | Webb | G01N 35/028 435/287.2 |
| 2003/0162285 A1 | 8/2003 | Tajima | |
| 2004/0023375 A1 | 2/2004 | Kornblith et al. | |
| 2004/0072722 A1 | 4/2004 | Kornblith et al. | |
| 2004/0077075 A1 | 4/2004 | Jensen et al. | |
| 2004/0086888 A1 | 5/2004 | Kornblith et al. | |
| 2004/0107986 A1 | 6/2004 | Neilson et al. | |

(56) References Cited

U.S. PATENT DOCUMENTS

| | | |
|---|---|---|
| 2004/0110301 A1 | 6/2004 | Neilson et al. |
| 2004/0121454 A1 | 6/2004 | Jury et al. |
| 2004/0197905 A1 | 10/2004 | Hafeman |
| 2005/0054028 A1 | 3/2005 | Teich et al. |
| 2007/0037285 A1 | 2/2007 | Ehret et al. |
| 2007/0087401 A1 | 4/2007 | Neilson et al. |
| 2008/0014571 A1 | 1/2008 | Teich et al. |
| 2008/0031774 A1 | 2/2008 | Magnant et al. |
| 2010/0227385 A1 | 9/2010 | Teich et al. |
| 2013/0040855 A1 | 2/2013 | Takayama et al. |
| 2014/0186876 A1 | 7/2014 | Teich et al. |

FOREIGN PATENT DOCUMENTS

| | | |
|---|---|---|
| DE | 44 05 375 | 8/1995 |
| DE | 101 36 005 | 11/2002 |
| DE | 103 29 983 | 3/2005 |
| EP | 0128438 A2 | 12/1984 |
| EP | 0 363 262 | 4/1990 |
| EP | 0402917 A2 | 12/1990 |
| EP | 0545284 A1 | 6/1993 |
| EP | 0 722 136 | 7/1996 |
| EP | 1416041 A4 | 8/2004 |
| EP | 2636452 A1 | 9/2013 |
| FR | 279233 | 10/2000 |
| WO | WO-8809808 A2 | 12/1988 |
| WO | WO-9308464 A1 | 4/1993 |
| WO | WO-9322678 A2 | 11/1993 |
| WO | WO-94/03583 A1 | 2/1994 |
| WO | WO-9429708 A1 | 12/1994 |
| WO | WO-95/22406 | 8/1995 |
| WO | WO-98/15645 | 4/1998 |
| WO | WO-99/55827 | 11/1999 |
| WO | WO-99/60630 | 11/1999 |
| WO | WO-00/32308 | 6/2000 |
| WO | WO-00/36410 | 6/2000 |
| WO | WO-0071669 A1 | 11/2000 |
| WO | WO-01/85901 | 11/2001 |
| WO | WO-02/00336 A2 | 1/2002 |
| WO | WO-02/02736 | 1/2002 |
| WO | WO-02/08385 | 1/2002 |
| WO | WO-02/11881 | 2/2002 |
| WO | WO-02/061858 | 8/2002 |
| WO | WO-02/072423 | 9/2002 |
| WO | WO-02/083852 | 10/2002 |
| WO | WO-02/099386 | 12/2002 |
| WO | WO-03/000557 | 1/2003 |
| WO | WO-03/004596 | 1/2003 |
| WO | WO-03/059518 A1 | 7/2003 |
| WO | WO-2004/065618 | 8/2004 |
| WO | WO-2004/094060 | 11/2004 |

OTHER PUBLICATIONS

International Preliminary Report on Patentability in PCT/US2013/069839 dated May 28, 2015 8 pages.

Isao Karube, "Microbial Sensor", Journal of Biotechnology, 15, (1990), pp. 255-266.

Klaus Riedel et al., "Microbial Sensors: Fundamentals and Application for Process Control", J. Chem. Tech. Biotechnol. 44, (1989), pp. 85-106.

Kraus et al. "Biosensing with Cellular Systems", Bioscope, 1, pp. 24-33, 1993.

Y.I. Korpan et al., "A Cell Biosensor Specific for Formaldehyde Based on pH-Sensitive Transistors Coupled to Methylotrophic Yeast Cells with Genetically Adjusted Metabolism", Analytical Biochemistry, 215, (1993), pp. 216-222.

Yicong et al., "Drug evaluations using a novel microphysiometer based on cell-based biosensors", Sensors & Actuators B 80:215-221 (2001).

"Footprint Dimensions", Society for Biomolecular Sciences SBS, ANSI American National Standards Institute, ANSI/SBS Jan. 2004, Jan. 25, 2006.

"How to Adjust pH Levels," Office Action mailed Sep. 28, 2010 in U.S Appl. No. 11/486,440.

The Nature of ATP, *ATP and Biological Energy*, (as printed from Internet on Oct. 4, 2005, http://www.emc.maricopa.edu/faculty/farabee/BIOBK/BioBookATP.html).

"Well Positions", Society for Laboratory Automation and Screening SLAS, ANSI American National Standards Institute, ANSI/SLAS Apr. 2004 (formerly recognized as ANSI/SBS Apr. 2004), Oct. 13, 2011.

Ainscow et al., "Top-down control analysis of ATP turnover, glycolysis and oxidative phosphorylation in rat hepatocytes," Eur. J. Biochem., 263(3):671-85 (Aug. 1999).

Amano et al., "Measuring respiration of cultured cell with oxygen electrode as a metabolic indicator for drug screening," Human Cell 12(1):3-10 (1999).

Andreescu et al., "Autonomous Multielectrode System for Monitoring the Interations of Isoflavonoids with Lung Cancer Cells," 76 Anal. Chem. 8, pp. 2321-2330 (2004).

Andreescu, S. et al., "Advanced electrochemical sensors for cell cancer monitoring," Methods, vol. 37 pp. 84-93 (2005).

B. Cunningham, P. Li, B. Lin, J. Pepper, "Colorimetric resonant reflection as a direct biochemical assay technique," Sensors and Actuators B, vol. 81, p. 316-328, Jan. 5, 2002.

Beebe D.J., Mensing G.A., Walker G.M. (2002) "Physics and applications of microfluidics in biology." Annu. Rev. Biomed. Eng., 4, 261-86.

Beebe D.J., Moore J.S., Bauer J.M., Yu Q., Liu R.H., Devadoss, C., Jo B.H. (2000) Functional hydrogel structures for autonomous flow control inside microfluidic channels. Nature, 404, 588-90.

Bousse, L., Cohen, C., Nikiforov, T., Chow, A., Kopf-Sill, A.R., Dubrow, R. and Parce, J.W. (2000) "Electrokinetically Controlled Microfluidic Analysis Systems." Annu. Rev. Biophys. Biomol. Struct. 29, 155-181.

Brecht & Gauglitz, "Optical probes and transducers," Biosensors and Bioelectronics, 10, p. 923-936, 1995.

Burd et al., "Tumor oxygenation and acidification are increased in melanoma xenografts after exposure to hyperglycemia and meta-iodo-benzylguanidine," Rediation Research 159:328-335 (2003).

Buttgereit et al., "A hierarchy of ATP-consuming processes in mammalian cells," Biochem. J., 1995 Nov. 15;312 (Pt 1):163-7.

Clark, L.C. Jnr. Ann. NY Acad. Sci. 1962; 102:29-45.

Criddle et al. "Simultaneous Measurement of Metabolic Heat Rate, CO2 Production, and O2 Consumption by Microcalorimetry" Analytical Biochem. 1991, 194:413-417.

De Beer, Dirk, "Micro-Electrodes." Immolilized Cells, Chapter 10 2001, 85-100. (mailed Feb. 2, 2012).

Deshpande et al., "Microplates with integrated oxygen sensing for medium optimization in animal cell culture," Cytotechnology 46:1-8 (2004).

Ekelund et al., "Microphysiometry: new technology for evaluation of anticancer drug activity in human tumor cells in vitro," Anti-Cancer Drugs 9:531-538 (1998).

Examination Report mailed Aug. 31, 2012 for European Patent Application No. 04788615.5 filed Sep. 8, 2004, 4 pages.

Extended European Search Report from EP Application No. 10184182.3.

Ferguson et al. "Simultaneous monitoring of pH, CO2, and O2 using an optical imaging fiber" Analytica Chemica Acta, 1997, 340: 123-131.

Flora K and J Brennan, "Comparison of Formats for the Development of Fiber-Optic Biosensors Utilizing Sol-Gel Derived Materials Entrapping Fluorescently-Labeled Proteins." Analyst, 1999, 124, 1455-1462.

Gatti et al., "Oxygen microoptodes: a new tool for oxygen measurments in aquatic animal ecology," Marine Biology, 2002, 140:1075-1085.

Ge X, Kostov Y, and G Rao. High Stability non-invasive autoclavable naked optical CO2 sensor. 2003. Biosensor and Bioelectronics 18:pp. 857-865.

Gesinski RM, Morrison JH, Toepfer JR. "Measurement of oxygen consumption of rat bone marrow cells by a polarographic method." *J Appl Physiol.* 1968; 24(6):751-754.

(56) References Cited

OTHER PUBLICATIONS

Gump et al., "TAT transduction: the molecular mechanism and therapeutic prospects," Trends Mol. Med., 13(10):443-48 (2007).
Guppy, J. Cell Phys. 170:1-7 (1997).
Handbook of Fluorescent Probes and Research Products published by Molecular Probes, Inc., Eugene, Oregon, USA, http://www.probes.com/handbook/ (accessed Mar. 12, 2004), Table of Contents, 2 pages.
Hasselbrink E.F. Jr., Shepodd T.J., Rehm J. (2002) "High-pressure microfluidic control in lab-on-a-chip devices using mobile polymer monoliths." Anal. Chem. 74, 4913-18.
Hua S.Z., Sachs F., Yang D.X., Chopra H.D. (2002) "Microfluidic actuation using electrochemically generated bubbles." *Anal. Chem.* 74, 6392-96.
Huber et al., "Direct optical immunosensing (sensitivity and selectivity)," Sensors and Actuators B, 6, p. 122-126, 1992.
International Preliminary Report on Patentability for PCT/US2004/029163, Dec. 15, 2005, 15 pages.
International Preliminary Report on Patentability for PCT/US2007/013998, Jan. 22, 2009, 12 pages.
International Search Report and Written Opinion for PCT/US2004/029163, Mar. 2, 2005, 12 pages.
International Search Report and Written Opinion for PCT/US2007/013998, Apr. 8, 2008, 19 pages.
International Search Report and Written Opinion for PCT/US2013/069839, Jun. 3, 2014, 9 pages.
International Search Report for International Application No. PCT/US03/38294, Apr. 2004.
Invitation to Pay Additional Fees & Partial Internation Search for International Application No. PCT/US2007/013998, mailed Feb. 1, 2008.
Jekabsons et al., "Bioenergetic analysis of cerebellar granule neurons undergoing apoptosis by potassium/serum deprivation," Cell Death Differ. 13(9):1595-610 (Sep. 2006) (Epub Jan. 20, 2006).
Jin et al., "A biosensor concept based on imaging ellipsometry for visualization of biomolecular interactions," Analytical Biochemistry, 232, p. 69-72, 1995.
Jordan & Corn, "Surface Plasmon Resonance Imaging Measurements of Electrostatic Biopolymer Adsorption onto Chemically Modified Gold Surfaces," Anal. Chem., 69:1449-1456 (1997).
Karasinski, J. et al., "Detection and identification of bacteria using antibiotic susceptibility and a multi-array electrochemical sensor with pattern recognition," Biosensors and Bioelectronics, vol. 22, pp. 2643-2649 (2007).
Lehmann, M, Baumann W, Brischwein M, Gahle H-J, Freund I, Ehret R, Dreschler S, Palzer H, Kleintges M, Sieben U and Wolf B. "Simultaneous measurement of cellular respiration and acidification with a single CMOS ISFET. 2001." Biosensors & Bioelectronics. 2001;16:195-203.
Linder, V., Sia, S., and Whitesides, G. "Reagent-Loaded Cartridges for Valveless and Automated Fluid Delivery in Microfluidic Devices." American Chemical Society 2005; 77(1):64-71.
Lou et al., "Mitochondrial uncouplers with an extraordinary dynamic range," Biochem J., 407(1):129-40 (Oct. 2007).
Ländesmäki I, Scampavia LD, Beeson C, and Ruzicka J. "Detection of Oxygen Consumption of Cultured Adherent Cells by Bead Injection Spectroscopy." *Anal. Chem.* 1999; 71: 5248-5252.
Maharbiz et al., "Silicon microbial bioreactor arrays," Poster 83, 1st Annual International IEEE-EMBS Special Topic Conference on Microtechnologies in Medicine & Biology, Oct. 12-14, Lyon, France.
McConnell, H.M., Owicki, J.C., Parce, J.W., Miller, D.L., Baxter, G.T., Wada, H.G. and Pitchford, S. (1992) "The Cytosensor Microphysiometer: Biological Applications of Silicon Technology" Science 257: 1906.
Metzger, R., Deglmann, C.J., Hoerrlein, S., Zapf, S. and Hilfrich, J. (2001) Toxicology 166, 97-108.
Morhard et al., "Immobilization of antibodies in micropatterns for cell detection by optical diffraction," Sensors and Actuators B, 70, p. 232-242, 2000.

Motterlini et. al., "Depression of Endothelial and Smooth Muscle Cell Oxygen Consumption by Endotoxin," American Journ. of Physio. vol. 275, No. 168 p. 776-782, Sep. 1998.
O'Riordan TC, Buckley D., Ogurtsov V, O'Connor R., Papkovsky DB "A cell viability assay based on monitoring respiration by optical oxygen sensor." *Anal. Biochem.* 2000; 278(2):221-227.
Office Action in Chinese Patent Application No. 200480029825, mailed Jul. 18, 2008.
Office Action in Chinese Patent Application No. 200480029825, mailed Nov. 28, 2008 (translation).
Office Action in Chinese Patent Application No. 200780031522.6, dated Feb. 1, 2011.
Office Action in Chinese Patent Application No. 200780031522.6, dated Jul. 15, 2010 (translation).
Office Action in Chinese Patent Application No. 200780031522.6, dated Jul. 29, 2011 (translation).
Office Action in Indian Patent Application No. 1170/DELNP/2006, mailed Oct. 6, 2008 (translation).
Official Action in European Patent Application No. 04788615.5-1234, dated Mar. 12, 2008, 4 pages.
Official Action in European Patent Application No. 04788615.5-1234, dated Sep. 8, 2010, 6 pages.
Owicki, J.C., Bousse, L.J., Hafeman, D.G., Kirk, G.L., Olson, J.D., Wada, H.G. and Parce, J.W. (1994) "The Light-Addressable Potentiometric Sensor: Principles and Biological Applications." Ann. Rev. Biophys. Biomol. Struct. 23: 87-113.
Paitan et al., "Monitoring Aromatics Hydrocarbons by Whole Cell Electrochemical Biosensors," Analytical Biochemistry, 335:175-183 (2004).
Panten U and Klein H. "O2 consumption by isolated pancreatic islets, as measured in a Microincubation system with a Clark-type electrode." Endocrinology 1982; 111:1595-1600.
Parce W, Owicki J, Kercso K, Sigal G, Wada H, Muir V, Bousse L, Ross K, Sikic B, and McConnell H. 1989. "Detection of Cell-Affecting Agents with a Silicon Biosensor." Science. 1989; 246(4927):243-247.
Pattison R, Swamy J, Mendenhall B, Hwang C, and Frohlich B. "Measurement and Control of Dissolved Carbon Dioxide in Mammalian Cell Culture Processes Using an in Situ Fiber Optic Chemical Sensor." 2000. Biotechnology Prog. 16:769-774.
Pouli, A.E., Karagenc, N., Arden, S., Bright, N., Schofield, G.S., Hutton, J.C. & Rutter, G.A. (1998) "A phogrin-aequorin chimaera to image Ca2+ in the vicinity of secretory granules." Biochem. J., 330, 1399-1404.
Prokop et al., "NanoLiterBioReactor: long-term mammalian cell culture at nanofabricated scale," Biomedical Microdevices 6(4):325-339 (2004).
Robiolio et al., "Oxygen diffusion and mitochondrial respiration in neuroblastoma cells," Am. J. Physiol. 256 (6 Pt 1):C1207-1213 (Jun. 1989).
Rumsey et al., "Cellular Energetics and the Oxygen Dependence of Respiration in Cardiac Myocytes Isolated from Adult Rat" Journal of Biological Chemistry. 265(5):15392-15399. 1990.
Scott et al., "Energy transduction in intact synaptosomes. Influence of plasma-membrane depolarization on the respiration and membrane potential of internal mitochondria determined in situ," Biochem. J. 186(1):21-33 (Jan. 1980).
Seaver et al. "Hydrogen Peroxide Fluxes and Compartmentalization inside Growing *Eschericha coli*"J. Bacteriol., 2001, 183: 7182-7189.
Shenoy MA, Biaglow JE, Varnes ME, Hetzel FW. "Inhibition of cultured human tumor cell oxygen utilization by chlorpromazine." Adv Exp Med Biol.1983;159:359-68.
Terada, "Uncouplers of oxidative phosphorylation," Environ. Health Perspect., 87:213-18 (1990).
Thorsen, T., Maerkl, S.J. and Quake, S.R. (2002) Microfluidic Large-Scale Integration Science 298, 580-586.
Tolosa L, Kostov Y, Harms P, Rao G. "Noninvasive measurement of dissolved oxygen in shake flasks." Biotechnol Bioeng Dec. 5, 2002;80(5):594-97.
Unger, M.A., Chou, H-P, Thorsen, T., Scherer, A, and Quake, S.R. (2000) Science 288, 113-116.

(56) References Cited

OTHER PUBLICATIONS

Van der Gun et al., "Serum insensitive, intranuclear protein delivery by the multipurpose cationic lipid SAINT-2," J. Control Release, 123:228-238 (2007).
Vanderkooi et. al., "An Optical Method for Measurement of Dioxygen Concentration Based upon Quenching of Phosphorescence, " J. Biol. Chem., 262 (12):5476-5482 (Apr. 1987).
Wada, H.G. Indelicato, S.R., Meyer, L. Kitamura, T., Miyajima, A., Kirk, G., Muir, V.C. and Parce, J.W. (1993) "GM-CSF Triggers a Rapid Glucose Dependent Extracellular Mediated Activation of Acid Production." J. Cell Physiol. 154: 129-138.
Wiley, C and Beeson, C. (2002) "Continuous measurement of glucose utilization in heart myoblasts." Analytical Biochemistry 304, 139-146.
Wilson et al., "The Oxygen Dependence of Mitochondrial Oxidative Phosphorylation Measured by a New Optical Method for Measuring Oxygen Concentration," J. Biol. Chem., 263:2712-2718 (1988).
Wodnicka M, Guarino RD, Hemperly JJ, Timmins MR, Stitt D, Pitner JB. "Novel fluorescent technology platform for high throughput cytotoxicity and proliferation assays." Journal of Biomolecular Screening. 2000; 5:141-152.
Wolfbeis OS, 2002. "Fiber-Optic Chemical Sensors and Biosensors." *Annal of Chem*. 2002; 74:2663-2678.
Yang et al., "Reversible and repeatable linear local cell force response under large stretches," Experimental Cell Research, 2005, Apr., 305:42-50.
International Search Report and Written Opinion in PCT/US2015/033815, dated Sep. 9, 2015, 10 pages.

\* cited by examiner

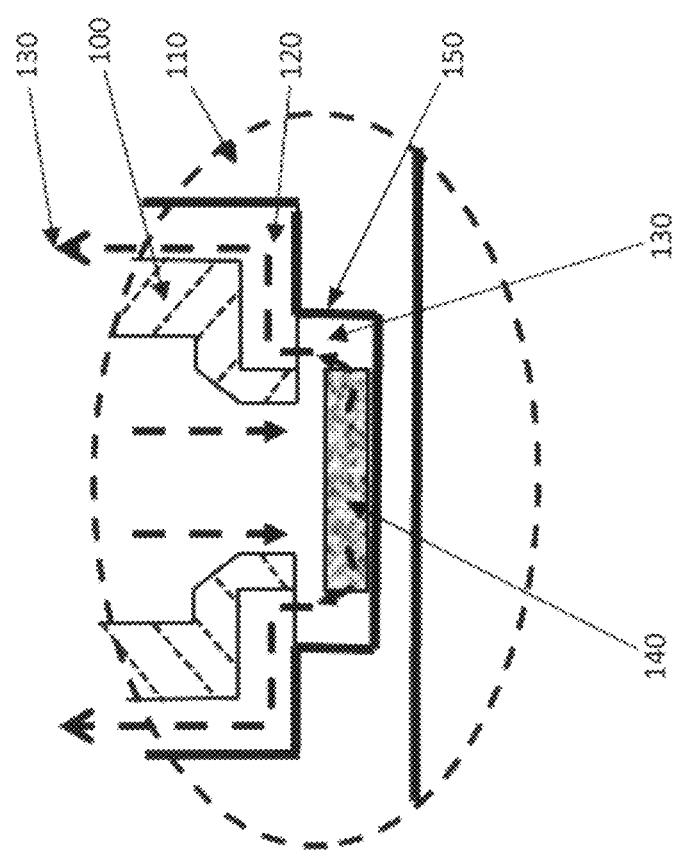

APPARATUS AND METHODS FOR THREE-DIMENSIONAL TISSUE MEASUREMENTS BASED ON CONTROLLED MEDIA FLOW

RELATED APPLICATION

This application claims the benefit of priority under 35 U.S.C. §119(e) to U.S. Provisional Application Ser. No. 61/725,781 filed Nov. 13, 2012, the entirety of which is incorporated herein by reference.

FIELD OF THE INVENTION

The invention relates generally to apparatus and methods for conducting analysis of three-dimensional cell samples (e.g., tissue samples).

BACKGROUND

It has long been established that distinct differences in the metabolic phenotype of cancer cells are linked to underlying mechanisms that provide a selective advantage for survival and proliferation. However, the precise mechanisms that trigger tumorgenesis are poorly understood. It has been postulated that glycolytic adaptation is a survival mechanism that allow tumors to proliferate in a microenvironment characterized by low pH and oxygen tension. These adaptations of "the Warburg shift" provide a selective advantage to the tumor through increased glucose uptake and ATP synthesis in order to meet the demands for biosynthesis, energy and reducing equivalents.

Recent advances in the development of instruments that measure the flux of key analytes indicating aerobic metabolism ($O_2$), glycolysis ($H^+$), and intermediary metabolism ($CO_2$) within the microenvironment may provide insight to the underlying mechanism of malignant transformation. However, these systems are designed and optimized for use in cell-based assays, may lack environmental control, and generally do not facilitate the measurement of multicellular tissue samples because of constraints on chamber size, difficulty in immobilization and perfusion of the sample.

Seahorse Bioscience, Billerica, Mass., launched the XF96 "Extracellular Flux Analyzer" in 2007. Since that time the product has been adopted as a technology platform for making quantitative measurements of mitochondrial function and cellular bioenergetics. XF measurements are performed in a fully integrated instrument that measures the concentrations of various analytes ($O_2$, $H^+$, $CO_2$) in the extracellular media of a cell based assay. Analyte concentrations are measured non-invasively, within a small volume about the cells, providing quantitative measurements for changes in analyte concentrations as a function of time from which bioenergetic flux (example: $dO_2/dt$=oxygen consumption rate, $dpH/dt$=extracellular acidification rate) can be determined. XF measurements are based on a method in which a small, temporary, measurement volume is created around the cells, or a sensor is placed in close proximity to the cells. Measurements under these conditions amplifies changes in concentrations allowing highly sensitive, time resolved measurements to be collected from a set of optical sensors. Once the measurement is made, the plunger (probe) is lifted and the medium around the cells is restored to its original condition. This nondestructive method allows multiple measurements to be serially collected for a biological sample under various conditions of stimulation (basal, environmental change, compound stimulus).

By measuring key metabolic parameters such as oxygen consumption rate (OCR) and extracellular acidification rate (ECAR), a profile of the bioenergetic phenotype may be developed based on the substrate and pathway (glycolysis or oxidative phosphorylation) for generating energy and biosynthesis. The product allows quantitative measurements of mitochondrial function and cellular bio-energetics of cells.

A need exists for a system that allows for measurement of key analytes of, for example, aerobic metabolism, glycolysis and intermediary metabolism in multicellular tissue.

SUMMARY OF THE INVENTION

The instrument and methods described herein allow the measurement of bioenergetic parameters in tissue samples or cell populations, e.g., tumor tissue samples, to generate its metabolic profile, thereby enabling, for example, a better understanding of the mechanisms of malignant progression. Accordingly, embodiments of the invention enable testing of physiologically relevant hypotheses that to date could not be tested otherwise, for example, by enabling the measurement and quantification of phenotypic shifts in tumors.

Embodiments of the invention comprise an apparatus for conducting analysis of three-dimensional cell samples. The apparatus may include a plate of wells that are loaded with tissue samples which are tested by placing the plate in a machine specifically adapted as disclosed herein to conduct assays in wells of the plate. The plate typically defines a plurality of wells for holding respective samples and sample media, where at least one of the wells, typically the entire array of wells, includes a sample nesting site disposed therein. A bore is disposed above the nesting site, the bore being dimensioned to interfit with a plunger that moves vertically down within the bore and within the sample media disposed in the well. In practice it is preferred to maintain the well(s) or well plate in position on a stage or platform and robotically move the plunger(s), but it is possible but not preferred to keep the plungers stationary and move the plate. The structure also defines a media channel that is in fluid communication with the sample nesting site. The media channel permits media displaced by the plunger to flow through and expose the sample to fresh media as the plunger moves.

One or more of the following features may be included. The plunger preferably moves relative to the nesting site to induce perfusion of media about the sample, preferably on both the down and up stroke. Alternatively, the plunger and sample nesting site may move together to expose the sample to different regions of media. The media channel may include a fluid path that returns media perfused about the sample back to media disposed in the well. The bore, sample nesting site, and/or media channel may be defined by a removable well insert.

The sample nesting site may include a media permeable platform defined by or as a part of the removable well insert. The well may include a sump in fluid communication with the media channel. The sample nesting site may be disposed within the sump where media collects and flows through the media channel.

The media channel may include a fluid path defining a closed loop beneath the surface of media in the well to permit media perfusive flow about the sample on both upward and downward movement of a plunger within the bore. A check valve may be included in the media channel to inhibit backflow of spent media from the channel to the sample during upward movement of the plunger.

The apparatus may include sensors for detecting the concentration of solutes secreted from or absorbed by the sample in the media disposed about the sample. The sensors may be disposed at the bottom of at least one of the wells. The sensors may comprise fluorophores sensitive to the concentration of one or more solutes in the media mounted on the plungers to measure in regions adjacent the tissue sample, for example, oxygen, $CO_2$ or $H^+$ concentration. The sensors may comprise beads coated with specific binders of specific cytokines, chemokines, hormones, or other biomolecules absorbed by or secreted from the tissue which become immobilized on the beads. The beads may be probed in situ in a sump in a well to enable detection of the concentrations of molecules of interest secreted or taken up by the tissue. Alternatively, the beads may be separated from the media and analyzed. In some embodiments, in place of beads, spotted antibodies may be disposed in a bottom portion of the well in fluid connection with the media perfusing through the well. The spotted antibodies may be used to detect other molecules of interest.

The apparatus may include plungers adapted for reciprocating movement within the bores of respective wells. In a preferred embodiment, fluorophore sensors may be disposed on the plungers for detecting the concentration of solutes in media disposed about the sample. The sensors may measure the concentration of oxygen, carbon dioxide, and/or hydrogen ions dissolved in media about the sample.

The plurality of wells may define a multi-well plate including, for example, 24 or 96 wells.

A source of oxygen, carbon dioxide, and/or a biologically inert gas may be in fluid communication with media in a well or a headspace above the surface of media in the wells for controlling the composition of gas in the headspace or in the media. A source of a solution of a biologically active substance may be in fluid communication with media in wells for exposing a sample to the substance.

A three-dimensional cell growth scaffold may be disposed on the sample nesting site.

In another aspect, embodiments of the invention may include an apparatus for conducting analysis of three-dimensional cell samples. The apparatus may include a well for holding a sample and sample media, the well including a sample nesting site. A bore may be disposed above the nesting site, the bore being dimensioned to interfit with a plunger that moves vertically down within the bore and within media disposed in the well. The apparatus may also include a media channel in fluid communication with the sample nesting site that permits media perfusion about the sample, and a plunger adapted for reciprocal movement in the bore to impel media perfusion about the sample.

The apparatus may optionally include a sensor for detecting the concentration of a dissolved media component in media about the sample nesting site.

In yet another aspect, embodiments of the invention feature an insert for a well of a culture plate for adapting the well to implement perfusion of a three-dimensional cell culture sample disposed therein. The insert includes a structure defining (i) a sample nesting site comprising a media-permeable platform, and (ii) disposed thereabove a bore dimensioned to interfit with a plunger which moves vertically down within the bore and within media disposed in a well. The insert may also define a media channel in fluid communication with the sample nesting site, which permits media perfusion about the sample impelled by a plunger.

In another aspect, the embodiments of the invention feature a method of experimenting with a three-dimensional cell culture sample, e.g., a tissue sample, biopsied sample, or cell scaffold holding cells, so as to maintain viability of the sample and exercise control over its microenvironment. The method includes providing a structure defining a well including a sample nesting site, a bore dimensioned to interfit with a plunger disposed above the sample nesting site, a media channel in fluid communication with the sample nesting site, and a plunger adapted for reciprocal movement in the bore. A sample is placed on the sample nesting site in medium within the well. The plunger is moved within the bore to impel media flow about the sample and through the channel to perfuse the sample with media.

One or more of the following features may be included. A gas may be added to the media or to headspace in the well above the media to modify the microenvironment about the sample by altering dissolved gas composition. A solution of a biologically active substance such as a drug, drug candidate, or toxin may be added to the media to modify the microenvironment about the sample by exposing the sample to the biologically active substance.

The concentration of one or more solutes in media about the sample may be measured. A plurality of measurements separated in time may be made of the concentration of one or more solutes in media about the sample.

A metered amount of one or more gases and/or one or more solutes may be added to media in the well thereby setting the microenvironment in the medium about the sample to a predetermined point. The microenvironment may be set to a hypoxic condition. An oxygen scavenger may be added to the medium.

A human biopsied tissue sample may be placed on the nesting site, potential therapeutic drugs may be added to the media, and the effect of the drugs on the sample may be assessed.

The sample may be a tumor sample, and a metered amount of one or more gases and/or one or more solutes may be added to media in the well thereby to set the microenvironment in the medium about the sample to a predetermined point simulating the microenvironment of the tumor sample in vivo.

The method may be multiplexed by providing a plurality of the wells including sample nesting sites, bores dimensioned to interfit with plungers disposed above the respective sample nesting sites, media channels in fluid communication with each of the sample nesting site, and plungers adapted for reciprocal movement in each of the bores. Sample may be placed on the sample nesting sites in media within each of a plurality of wells. The plurality of plungers may be moved within the bores to impel media flow about the samples and through the channels thereby to perfuse the samples with media. The concentration of one or more solutes in media about the samples in the plurality of the wells may be measured one or more times.

BRIEF DESCRIPTION OF THE DRAWINGS

FIGS. 1e and 1f are schematic cross sectional views of two embodiments of the lower portion of a single well of a multi-well plate with an insert disposed therein, showing a sample nesting site in a sump at the bottom of the well (1e), and a sample nesting site (and nested scaffold) disposed on a screen at the bottom of the insert (1f).

DETAILED DESCRIPTION

Figure 1B:
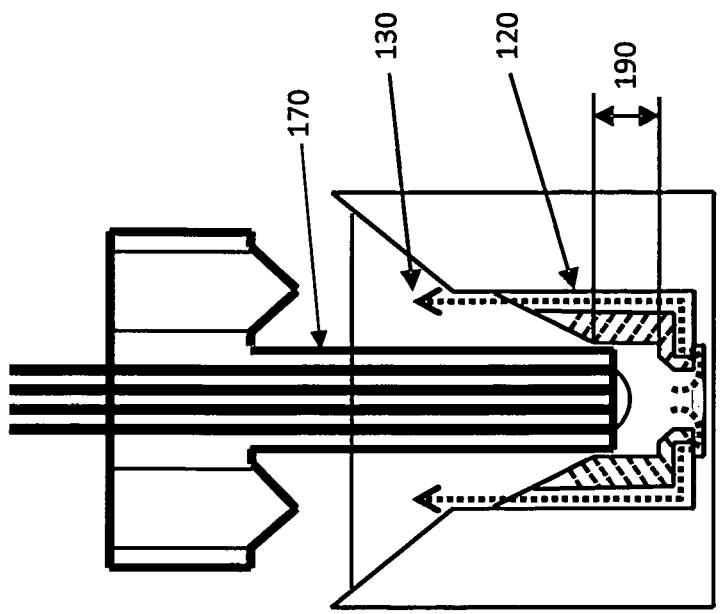
FIGS. 1a and 1b, are schematic, cross sectional views of a single well of a multi-well plate, with a plunger in the down position (1a) and up position (1b) and an insert disposed therein, in accordance with an embodiment of the invention.

Embodiments of the invention enable the measurement of one or more properties of one or more three-dimensional cell samples (e.g., tissue samples, biopsied samples, or cell scaffolds holding cells) that are disposed in, for example, one or more wells of a multiwell plate. Plates of various specific forms embodying the invention and well inserts that adapt more conventional plates to structures embodying the invention may be designed by the skilled artisan in view of this disclosure, and may be manufactured using conventional molding techniques from polymeric materials such as polyethylene terephthalate or polystyrene.

FIGS. 1a-1g show removable inserts 100 alone (FIG. 1d) or in place within a well 110, e.g., a single well of a multiwell plate. The insert may define media perfusion channels 120 to facilitate perfusion 130 of media over a three-dimensional cell sample, e.g., tissue 140 disposed in the well. The channels may comprise multiple passages formed within the body of the insert itself, or more preferably, comprise passages defined between the inner surface of the well and outer surface of the insert. The perfusion channels may include a check valve which functions to limit backflow of media from the channels to the sample on the upward stroke of the plunger. The insert may also include a sample nesting site 150 to receive a sample prior to insertion of the insert into the well. The sample nesting site, in some embodiments, is disposed in the well itself, e.g., in a depression or sump independent of the insert. The insert or the body of the well itself defines a bore 150 which interfits with a plunger 160. The plunger 160, well 110, and bore 150 are configured and dimensioned to fit together preferably so that insertion and reciprocation of the plunger into the well permits agitating and mixing of the medium. The plunger and the bore fit together to induce perfusion as the plunger moves downwardly or upwardly and medium perfuses the sample and passes through the perfusion channels. In some embodiments, the plunger also may be configured to introduce one or more sensors 180 for monitoring the presence or concentration of one or more analytes in medium disposed in the well. Information from the sensors 180 may be transmitted through a fiber-optic probe 182 disposed in the plunger 170. In some embodiments, a compound delivery structure 185 may be disposed above the well, enabling the introduction through, e.g., delivery ports, into the well of a biologically active substance or a gas into media surrounding the three-dimensional sample.

These elements of embodiments of the invention will now be discussed in detail. The bottom surface of the well 110 may define a depression that acts as a sump during use. The depression may be used to orient and control the positioning of samples in the well and its bottom surface to serve as a sample nesting site 150. The well may be one of many wells of a multiwell plate, that may be designed to a standard "Society for Biological Screening" SBS footprint having a 6 mm well diameter with the depression at the bottom of the well having a depth of, e.g., 0.5 mm and a diameter of, e.g., 3 mm. The dimensions of the depression may be selected in view of the analysis to be performed in the well. For example, the volume should be sufficient to hold a sample. The exemplary dimensions indicated above are suitable for holding a sample that is approximately 300 μm thick. Other dimensions may be provided, depending on analytical needs.

The removable insert 100 may be generally cylindrical, and sized and configured to slide into the well with a slight interference fit to its interior wall. See FIG. 1d. For example, the insert may have a height h1 of about 0.2 inches and an outer diameter OD of about 0.247 inches. The height of the insert may be selected such that that the stroke distance defined by the length of the bore in which the plunger generates hydrostatic pressure, i.e., perfusion stroke 190, may be increased or decreased to control the perfusion volume. The outer diameter of the insert may be selected to allow the insert to fit snugly in the well. For example, protrusions 195 may be disposed on the outer sidewall of the insert to help secure and center the insert in the well, providing an outer diameter OD' at some points of 0.251 inches. The top edge of the insert may be thin, e.g., have a thickness t1 of 0.002 inches, so as to aid in guiding the plunger into the insert. The inner surface of the insert may have an upper tapered portion and a lower vertical portion defining a bore having a diameter d1 of, e.g., 0.15 inches. The upper tapered portion may define an opening having a diameter d2 of e.g., 0.1 inches. The bottom of the bore of the insert may define an opening having a diameter d3 of, e.g., 0.080 inches. The opening may include a media permeable platform, e.g., a screen, sized and located to support a scaffold holding a three-dimensional cell culture or tissue sample. The insert defines a plurality of perfusion channels 120 that begin on the bottom of the insert and extend up the insert's outer diameter wall to form a channel such that fluid pumped through the opening having a diameter d3 during the downward stroke of the plunger can be exhausted to create perfusion across a sample. Each perfusion channel may have a height h2 of, e.g., 0.004 inches.

One currently preferred set of dimensions would define a 3 mm plunger stroke within a 3 mm bore so that the displaced volume of the pump (a bit over 20 mm3 or 20 μl) is approximately 4 times the volume of the channels. Accordingly, as currently contemplated, the plunger and insert are sized such that the plunger moves at least 20 μl of media when inserted into the bore. The smaller the clearance between bore and plunger the better the pump efficiency, so a minimum clearance of 0.001 inch and a maximum of 0.01 inch is a reasonable range. Larger clearances are contemplated in some embodiments to permit fresh media to flow downwardly around the piston on its upward stroke, particularly in embodiments including a check valve function as described below.

Referring to FIG. 1e, the snug fit of the insert 100 in the well 110 enables the insert to be held securely in place and, in use, may immobilize and orient the sample 140 in a sample nesting site 150 disposed in a small microchamber or sump formed by the interface created by the depression at the bottom of the well and a bottom portion of the insert. As shown, the sump is in fluid communication with the perfusion channel 120, i.e., with the media channel, through which perfusion flow 130 takes place. In some embodiments (not shown), the media channel may lead to a drain for collection of spent media. Thus, in some embodiments, media may be moved by the media channel to a waste site rather than back into the well.

As discussed hereinafter in more detail, including with reference to FIG. 1f, in other embodiments, the sample nesting site 150 is disposed on the insert 100 itself. For example, the insert may comprise a screen 190 at the bottom of the bore 160, on which a tissue sample or scaffold 200 with cells may be placed. In still other embodiments (not shown), the sample nesting site may be disposed on the plunger, e.g., rigidly suspended from its bottom surface, such that the sample nesting site moves together with the plunger to expose the sample to different regions of media. Accordingly a possible but not preferred configuration includes the suspension of the sample nesting site on the plunger.

Figure 1A:
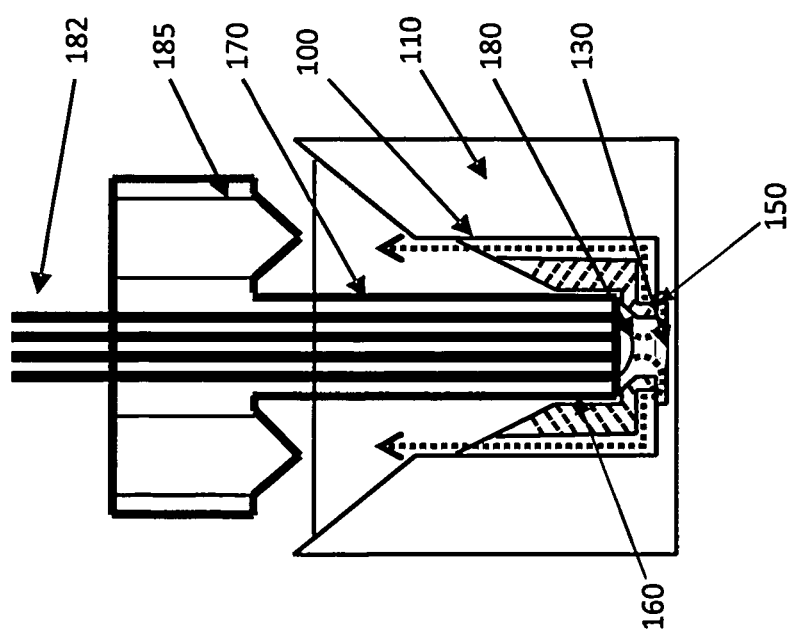
Figure 1C:
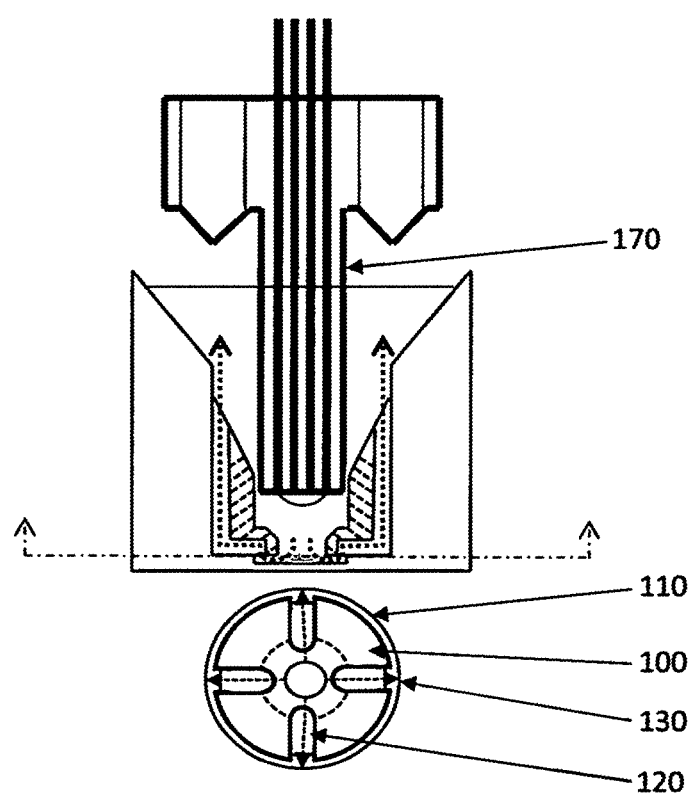
FIG. 1c shows the bottom of the insert in cross section.
Figure 1D:
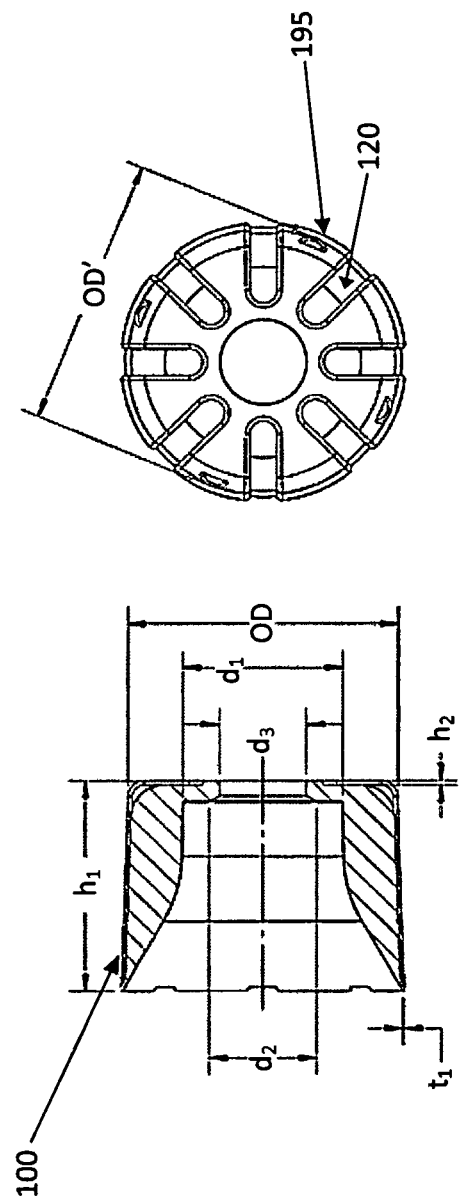
FIG. 1d is a schematic cross-sectional view of an insert and a bottom portion of the insert in accordance with an embodiment of the invention showing certain currently preferred dimensions.

Media channels that may be defined by the insert permits media displaced by the plunger to leave the proximity of the sample, e.g., by flowing up the perimeter walls through the annulus defined by an outer surface of the insert and an inner sidewall of the well. In some embodiments (not shown) the media channel may extend from a bottom portion of the insert to a higher portion of the insert. Referring to FIG. 1c, in an exemplary embodiment, the media channel may include a plurality, e.g., four, perfusion channels 120 defined in a bottom portion of the insert 100. The perfusion channels may be indentations defined on a bottom surface of the insert. Alternatively, perfusion channels may be cylindrical openings defined in the bottom portion of the insert. Each of the media channels may define a fluid path that returns media perfused about the sample back to media disposed in the well, or alternatively to a waste reservoir. The media channels are in fluid communication with the sample nesting site, permitting flow of media therethrough. The flow of media is impelled by the plunger 170, thereby permitting exposure of the sample to fresh media as the plunger moves.

Figure 1F:
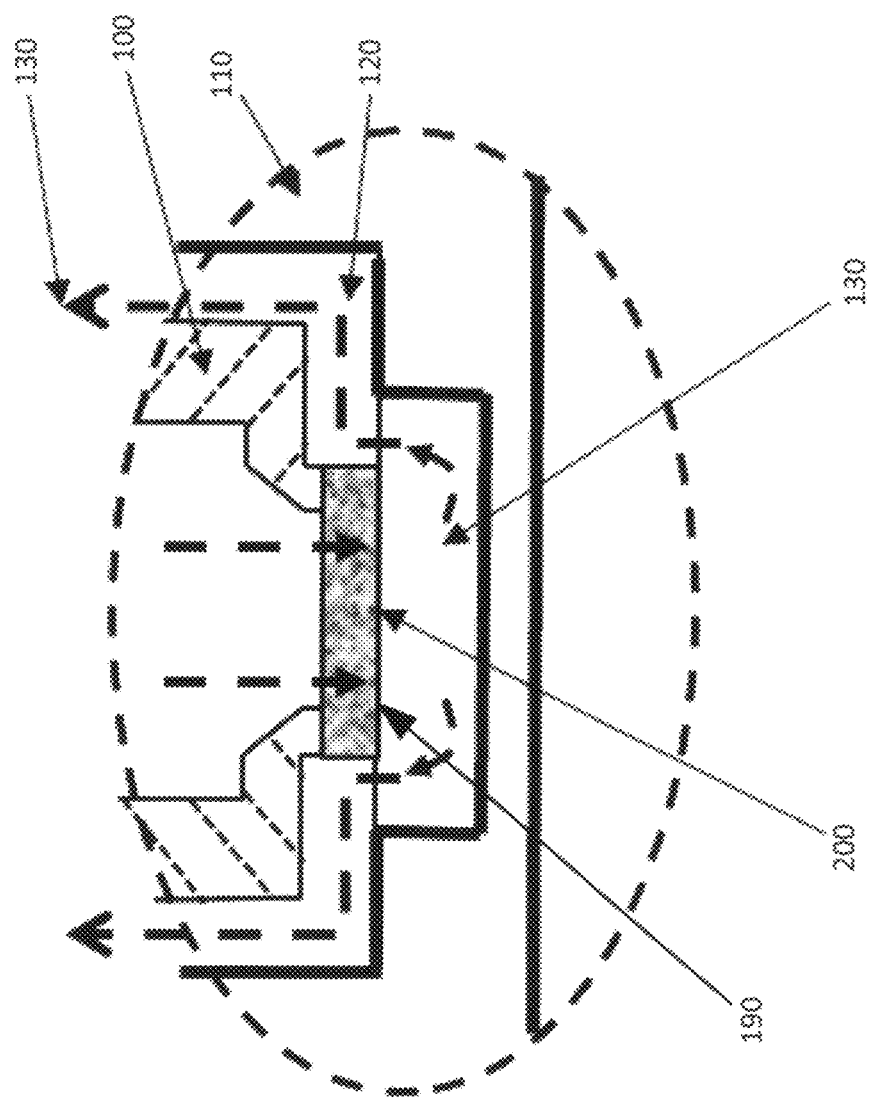

Referring to FIG. 1f, the insert may include the sample nesting site 150. For example, the insert may include a media permeable platform, such as a screen 190, spanning the opening in a bottom surface of the insert. The screen may be made from any number of materials, such as polymers such as polyethylene terephthalate (PET) or polystyrene, cellulose, paper, etc., and attached by ultrasonic welding, heat staking, adhesives or mechanical entrapment. In certain embodiments, adhesion of the sample to the nesting site may be enhanced by using attachment promoters or tissue adhesives, such as MatriGel™ or Cell-Tak™. In an alternative embodiment, as noted above, the sample nesting site may be within the depression at the bottom of the well.

Each of the media channels may include a fluid path defining a closed loop beneath the surface of media in the well, permitting media perfusive flow about the sample on both upward and downward movement of the plunger within the bore.

The insert may be fabricated by injection molding. Surface wettability may be increased by treatments known per se, e.g., performing a plasma pretreatment of the inserts to eliminate entrapment of gas bubbles in the perfusion channels by creating a more hydrophilic surface.

The bore preferably is situated above the nesting site, guides the plunger vertically down into the insert within the sample media disposed in the well, and creates hydrostatic pressure and media movement about the sample. Thus, the plunger may be adapted for reciprocating movement within the bore disposed in the well, e.g., the bore defined by the insert. FIG. 1a illustrates a plunger 170 extended into the bore 160, in close proximity to the sample, while FIG. 1b illustrates the plunger 170 somewhat retracted. As the plunger moves up and down along a distance defining a perfusion stroke 190, a volume of media is forced via hydrostatic pressure across the tissue or scaffold and up (or down) the perimeter walls between the insert and the inner surface of the well.

Figure 1G:
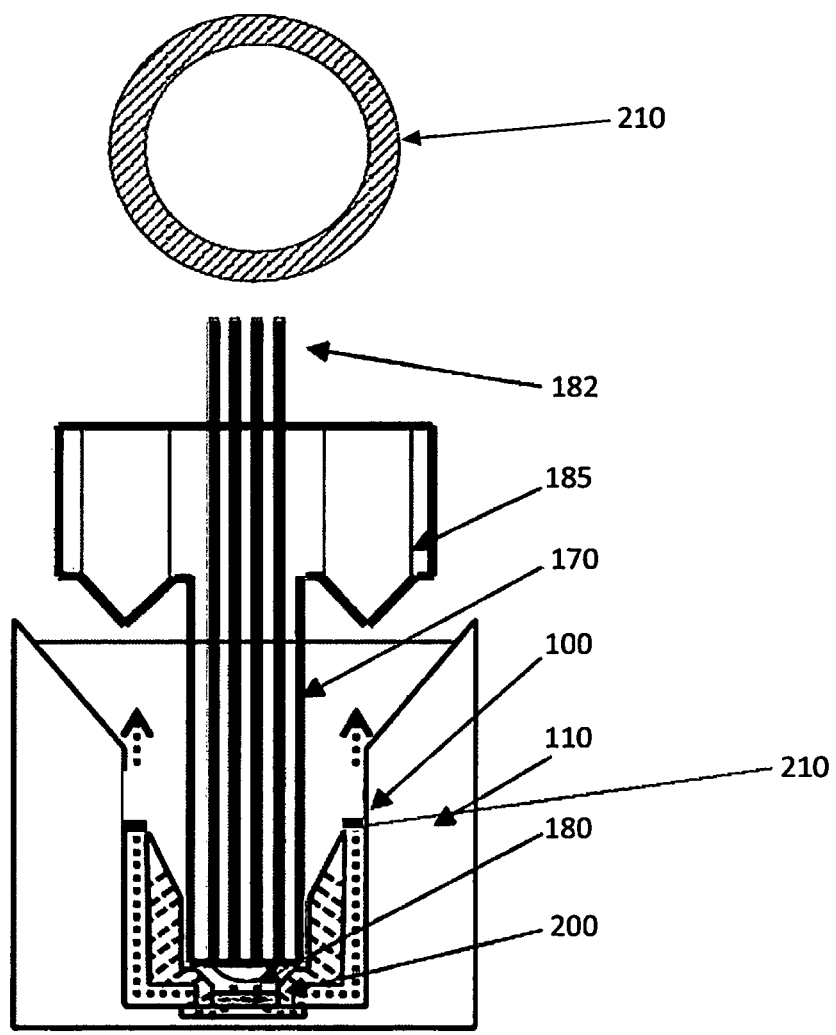
FIG. 1g is a schematic cross-sectional view of the structure of an alternative embodiment of the well of the invention showing a ring which acts as a check valve to inhibit backflow of spent media from the media channel to the sample site during upward movement of the plunger.

FIG. 1g shows one form of a check valve 210 for inhibiting backflow of media from the perfusion channels to the sample on upstroke of the plunger. The optional check valve 210 takes the form of a free floating annular ring comprising, e.g., an elastomeric polymer, that fits over the annular opening of the channels within the body of culture medium. On the downward stroke, hydrostatic pressure from the channels displaces the ring and permits flow of spent media upwardly and radially inwardly to mix back into the volume of media in the well. On the upward plunger stroke suction holds the ring in substantial sealing engagement with the opening of the channels, inhibiting media backflow from the channel. Medium accordingly is drawn down around the plunger through the annular clearance space between the plunger and the bore. Other check valve arrangements are contemplated, and the check valve function may be omitted if some backflow of media is tolerable. Still another alternative to a check valve for inhibiting back flow is to dispense with recirculation of spent medium, and to design the perfusion channels for one way drainage into a reservoir in the body of the well plate (not shown).

In some embodiments, the sample nesting site may include a scaffold 200 attached to the insert or to the bottom of the sump. A scaffold is a three-dimensional porous solid such as a collagen membrane that mimics the parenchyma of tissue and its surrounding structure in vivo. Such scaffolds are available commercially and may be fabricated from gels or fibrous/porous media, e.g., Alvetex® Scaffold or 3D BioTek scaffold material. Alvetex® Scaffold is a highly porous, cross-linked polystyrene scaffold that has been section into 200 µm thick membrane. The resulting material is inert and does not degrade during normal use. It has been adapted to fit a variety of conventional cell culture plasticware formats. Alvetex® Scaffold provides a suitable 3D structure in which cells can proliferate, migrate, differentiate, and function in an appropriate niche environment. Cells maintain a 3D shape and form close interactions with adjacent cells.

Figure 2:
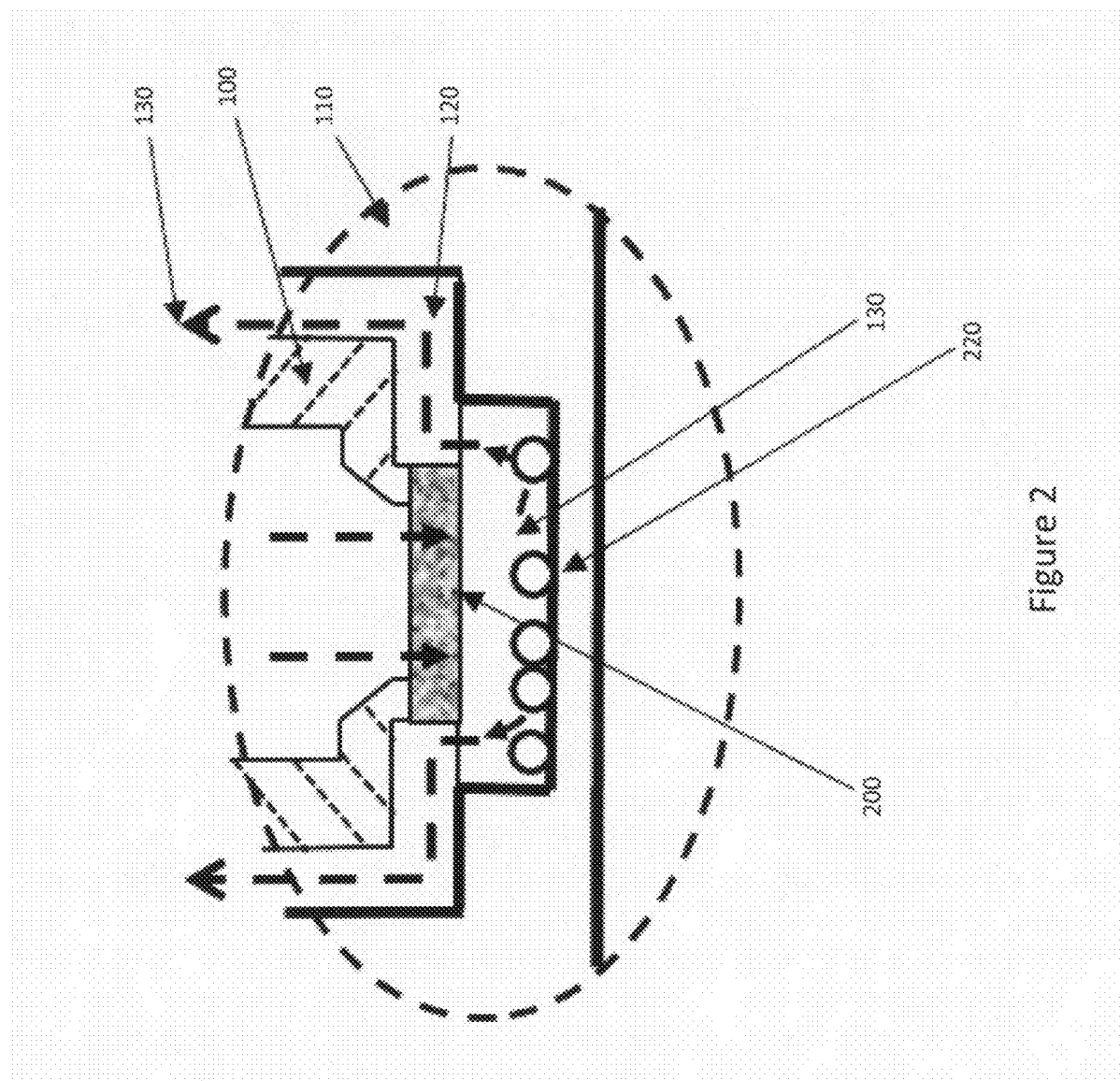
FIG. 2 is a schematic cross sectional view of the lower portion of a single well of a multi-well plate with an insert disposed therein and a sample nested on the insert, showing beads for detecting biomolecules present in media perfused from the tissue sample disposed in the sump.

Referring to FIG. 2, in an alternative embodiment, beads 220 comprising specific binders to biomolecules of interest may be disposed in the well 110 beneath or adjacent the sample as a means to assist with sample analysis. In particular, the scaffold 200 or tissue may be immobilized to the insert so that media can perfuse through and around it. In this arrangement, the media contains, for example, key nutrients, signaling molecules, drugs, etc. Beads such as are available from Luminex® containing an attachment molecule may be placed at the bottom of the well, such that multiple signaling molecules may be captured and subsequently detected or quantitated. One may take advantage of the sump and small volume of media in intimate contact with the sample effectively to amplify the concentration of the signaling molecules and to capture them on the beads. The beads preferably stay at the bottom of the well because they are trapped between the scaffold and the small channels around the perimeter. At the end of the assay, the insert or array of inserts may be removed, and the beads can be read using known techniques, e.g., analyzed in a flow cytometer.

The apparatus preferably includes sensors 180, in addition to the optional beads described above, e.g., disposed on the plungers, for detecting the concentration of solutes in media disposed about the sample. The sensors may measure the concentration of dissolved oxygen, carbon dioxide, or hydrogen ions in media about the sample. Measurements spaced in time permit assessment of the health or metabolic efficiency of the sample under various condition of its microenvironment.

Figure 3:
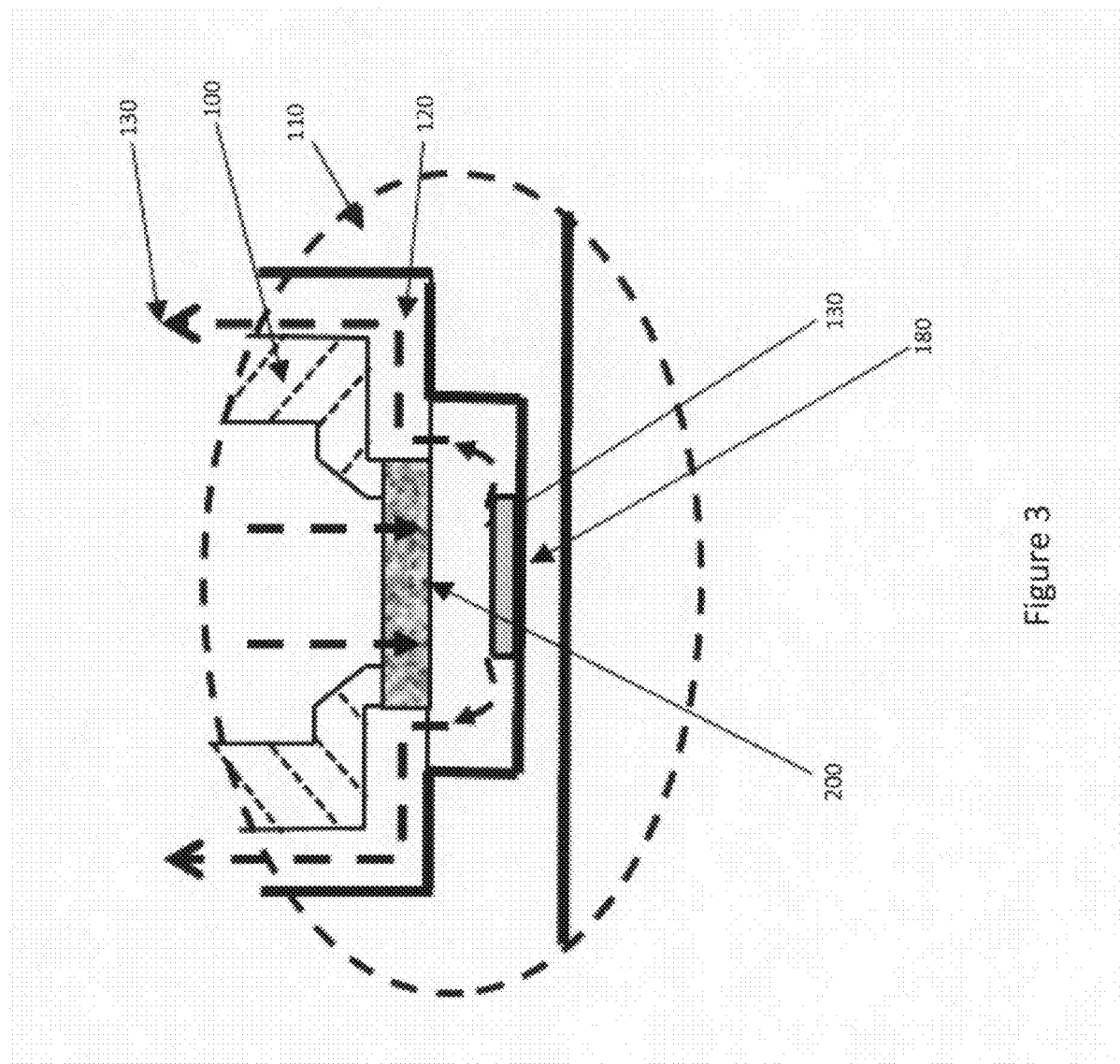
FIG. 3 is a schematic cross sectional view of the lower portion of a single well of a multi-well plate with an insert disposed therein, a sample nested on the insert ("3D scaffold"), and a sensor disposed at the bottom of the well in a sump.

Referring to FIG. 3, sensors 180 may be placed at the bottom of a well or the sump to detect the concentration of solutes in the media For example, one may dispose an $O_2$ or a pH sensor in the space between the bottom of the insert 100 and the bottom of the well 110. Plates with sensors are commercially available, but the drawback is that one has to grow the cells on the sensor. Kits with water soluble sensors to put into the media are also available, but also present disadvantages. The embodiment described herein allows microwell plates to be provided with sensors on the bottom and an insert thereabove, allowing the microwell plate to be read in a standard plate reader, e.g., the BioTek Synergy line of plate readers. These types of sensor configuration may be used with scaffolds or two- or three dimensional cultures grown on a membrane.

Various types of sensors may be utilized with the apparatus depending on the analysis to be performed and its selected configuration, including oxygen sensors, such as oxygen-quenched fluorescent sensors, pH sensors, including fluorescent sensors, ISFET and impedance sensors, $CO_2$ sensors, including bicarbonate buffer coupled and ammonium dye coupled fluorescent sensors as well as other $CO_2$ sensors; various ion and small molecule sensors; large molecule sensors including surface plasmon resonance sensors and sensors exploiting the principle of Wood's anomaly; acoustic sensors; and microwave sensors. In certain embodiments, a conventional plate reader may be used.

Preferred sensors are fluorophores. Many fluorescent sensing compounds and preparations are described in the art and many are available commercially from, for example, Molecular Probes Inc. and Frontier Scientific, Inc. The currently preferred oxygen sensor is a fluorophore with the signal inversely proportional to oxygen concentration such as a porphyrin or rhodamine compounds immobilized as a particle or homogenously distributed in an oxygen permeable polymer, e.g., silicone rubber. The currently preferred compound is porphyrin. The currently preferred pH sensor is a fluorescent indicator dye, fluorescein, whose signal decreases upon protonation of the dye, and which is either entrapped in a particle that is suspended in a carrier polymer, or covalently attached to a hydrophilic polymer. Useful fluorescent $CO_2$ indicator sensor typically are based on a pH sensitive transducer, with the fluorescence being indirectly modulated by the production of carbonic acid due to reaction of carbon dioxide with water. See, e.g., O. S. Wolfbeis, Anal. Chem. 2002, 74, 2663-2678. A fluorophore that detects glucose also can be used, such as one based on a non-enzymatic transduction using a boronic probe that complexes with glucose, resulting in a charge transfer that modulates the fluorescence of the probe, or an enzymatic glucose transducer that couples a glucose oxidase to a fluorescent oxygen sensor, with the binding and oxidation of glucose resulting in a quantitative modulation of the oxygen sensor. It also is within the scope of embodiments of the invention to employ a fluorophore or other type of sensor sensitive to biological molecules such as, for example, lactate, ammonia, or urea. A lactate sensor can be based on an enzymatic sensor configuration, with lactate oxidase coupled to a fluorescent oxygen sensor, and with the binding and oxidation of lactate resulting in a quantitative modulation of the oxygen sensor. An ammonia or ammonium ion sensor can be configured with immobilization of a protonated pH indicator in a hydrophobic, gas permeable polymer, with the fluorescence output quantitatively modulated by reaction with transient ammonia. A urea sensor can be based on an enzymatic sensor configuration, with urease coupled to a fluorescent ammonia transducer, and with the binding and reduction of urea to ammonia, resulting in modulation of the ammonia sensor fluorescence. The nature of the sensor generally does not form an aspect of embodiments of this invention.

In use, the insert guides the plunger to provide perfusion by creating hydrostatic pressure in the column of medium above the tissue sample in the insert and/or in the depression at the bottom of the well. As the plunger reciprocates vertically through the column, medium is forced to flow across and sometimes through the tissue and exits the chamber through a series of channels around the perimeter of the insert and upwardly between the outer surface of the insert and the inner wall of the well. By moving the plunger up and down, medium is moved across the tissue, replenishing nutrients, providing oxygen, and sweeping away wastes. Accordingly, the microenvironment around the sample may be continuously perfused between measurements. As the plunger moves into the bottom position, resting on or just above the insert, its motion is stopped, the small transient volume is created, and measurements are made. Efficiency of perfusion through the insert may be increased by altering the stroke height, speed and clearances between the plunger and the insert.

Figure 4A:
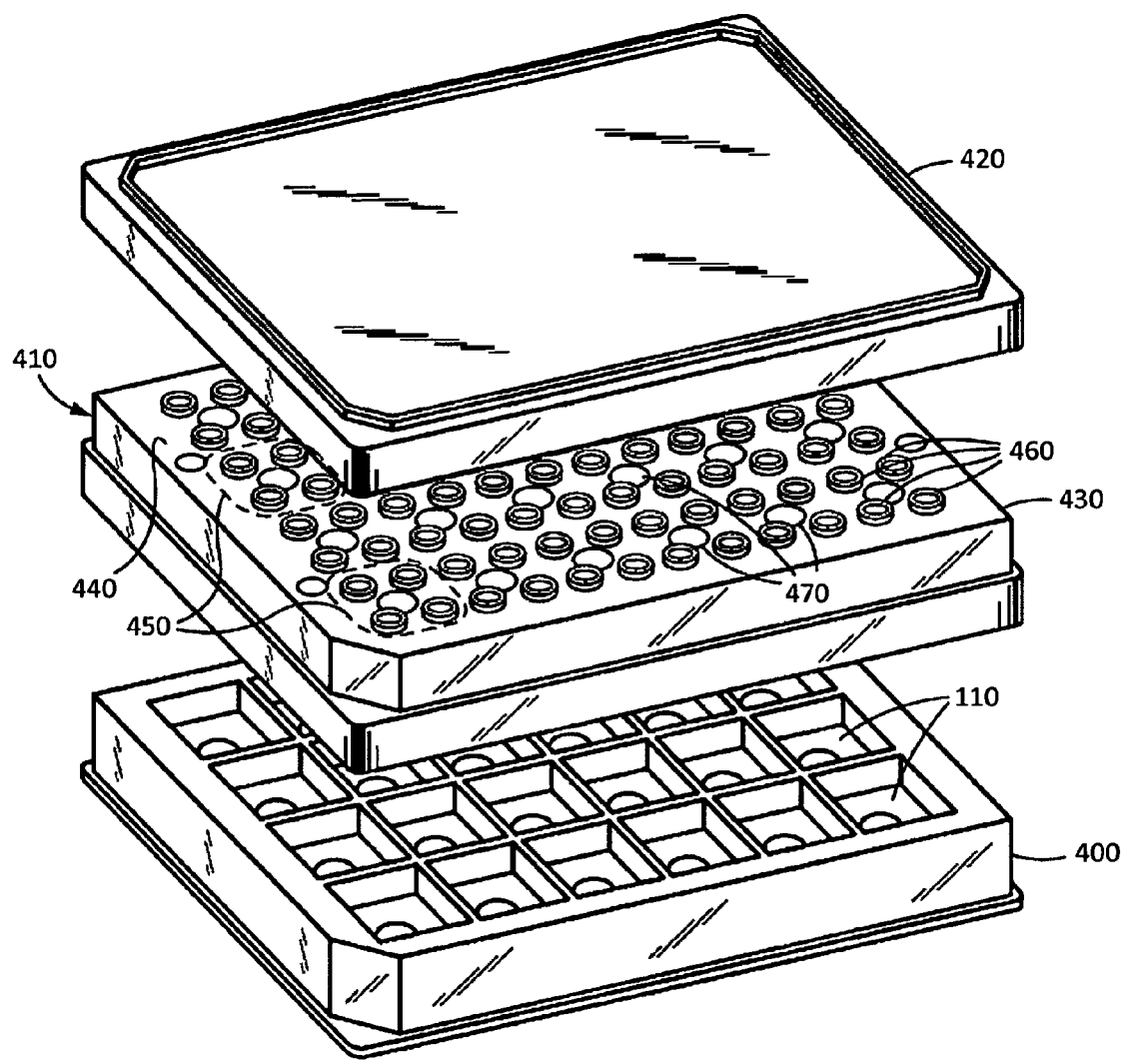
FIGS. 4a and 4b are upright and inverted (respectively) exploded perspective views of a multi-well plate and a covered cartridge adapted to mate with the plate showing various features of the plate in accordance with an embodiment of the invention.
Figure 4B:
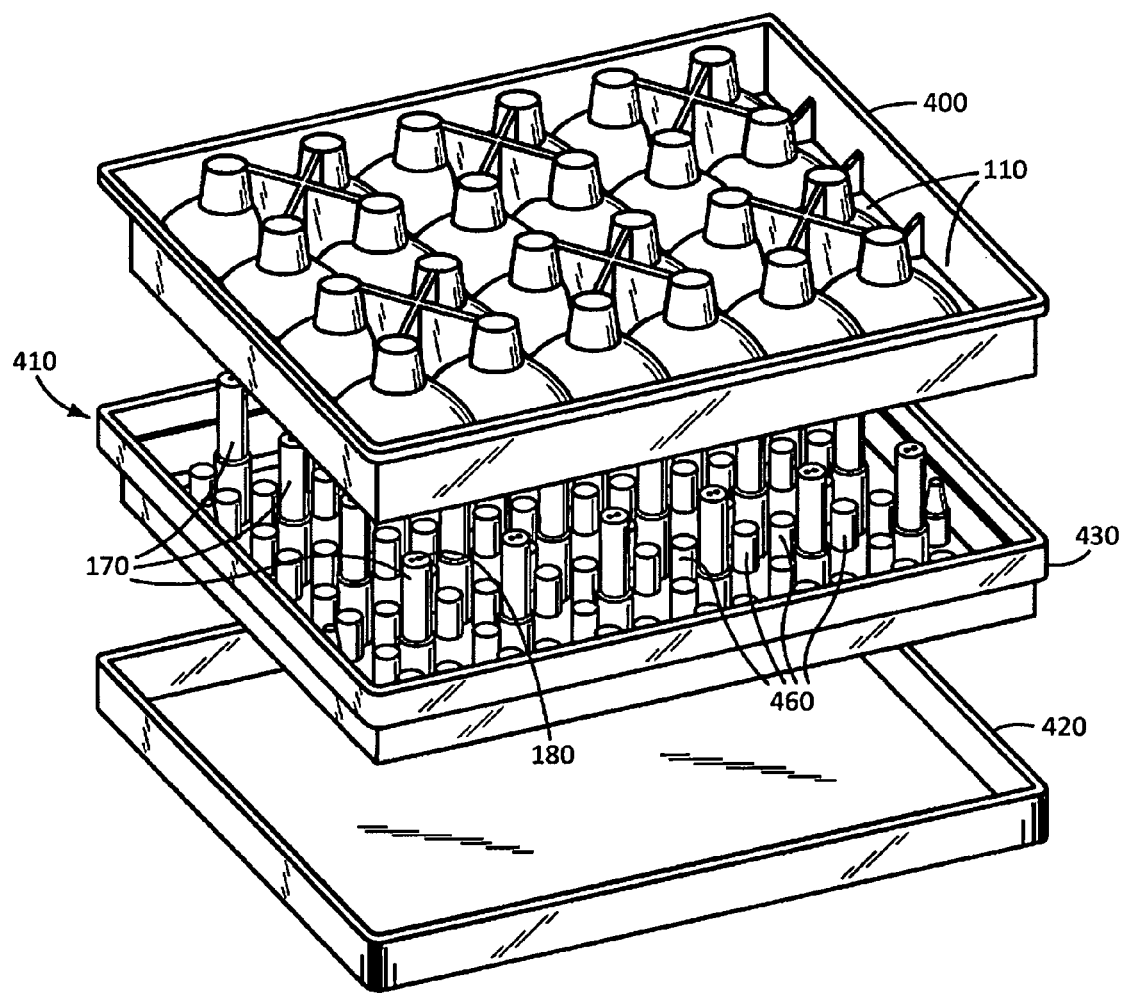

Referring to FIGS. 4a and 4b, a well plate configuration suitable for receiving the inserts described above and practicing embodiments of the invention is shown. It comprises a wellplate 400 defining a plurality of wells 110. The wellplate may be combined with a cartridge 410 and removable cover 420. In the depicted embodiment, multiwell plate 400 has 24 wells. The number of wells 110 in a plate may vary from 1 to several thousand. In some embodiments, a single well of nearly any size may be fabricated, or multiple wells may be fabricated, or multiple wells may be fabricated in a one- or two-dimensional arrangement. In various embodiments, one may exploit a two-dimensional pattern of wells corresponding to the pattern and dimensions of a microplate as described for example by the Society for Biomolecular Screening standards for microplates ("SBS-1 Footprints" and "SBS-4 Well Positions," both full proposed standards updated May 20, 2003). The plates may comprise 12, 24, 96, 384, 1536, or any other number of individual wells. The larger numbers of wells present engineering challenges because of the fine structure required to practice embodiments of the invention. The cartridge 410 is a generally planar element comprising a frame 430 made, e.g., from molded plastics. Planar surface 440 defines a plurality of regions 450 that correspond to, i.e., register with, a number of the respective openings of a plurality of wells 110 defined in the multiwell plate 400. Within each of these regions 450, in the depicted embodiment, the planar element defines first, second, third, and fourth ports 460, which serve as reservoirs for delivery of gases or reagents, and a central aperture 470 to a plunger 170. Each of the ports is adapted to hold and to release on demand a test fluid to the respective well 110 beneath it. The ports 460 are sized and positioned so that groups of four ports may be positioned over the wells 110, and a gas or test fluid from any one of the four ports may be delivered to a respective well 110. In some embodiments, the number of ports in each region may be less than four or greater than four. The ports 460 and plungers 170 may be compliantly mounted relative to the microplate 400 so as to permit it to nest within the microplate by accommodating lateral movement. The construction of the microplate to include compliant regions permits its manufacture to looser tolerances, and permits the cartridge to be used with slightly differently dimensioned microplates. Compliance can be achieved, for example, by using an elastomeric polymer to form planar element 440, so as to permit relative movement between frame 430 and the plungers and ports in each region.

Each of the ports 460 may have a cylindrical, conic or cubic shape, open through planar element 430 at the top, and closed at the bottom except for a small hole, i.e., a capillary aperture, typically centered within the bottom surface. The capillary aperture is adapted to retain test fluid in the port, e.g., by surface tension, absent an external force, such as a positive pressure differential force, a negative pressure differential force, or possibly a centrifugal force. Each port may be fabricated from a polymer material that is impervious to gasses, test compounds, or from any other solid material. When configured for use with a multiwell microplate 400, the liquid volume contained by each port may range from 500 µl to as little as 2 µl, although volumes outside this range are contemplated.

Referring to FIG. 4b, in each region of the cartridge 110, disposed between and associated with one or more ports 460, is a submersible plunger 170 (i.e., sensor sleeve or barrier), adapted to be disposed in the corresponding well 110. Plunger 170 may have one or more sensors 180 disposed on a lower surface thereof for insertion into media in a well 110. The sensor can be used to detect the concentration of a dissolved media component in media about the sample nesting site. One example of a sensor for this purpose is a fluorescent indicator, such as an oxygen-quenched fluorophore, embedded in an oxygen permeable substance, such as silicone rubber. The fluorophore has fluorescent properties dependent on the presence and/or concentration of a constituent in the well 110. Other types of known sensors may be used as described above, such as electrochemical sensors, Clark electrodes, etc. Plunger 170 may define an aperture and an internal volume adapted to receive a sensor.

The cartridge 410 may be attached to the plunger, or may be located proximal to the plunger without attachment, to allow independent movement. The cartridge 410 may include an array of compound storage and delivery ports assembled into a single unit and associated with a similar array of plungers.

The apparatus may also feature a removable cover 420 for the cartridge 110 or for multiwell plate 400. The configuration of cartridge 110 as a cover for multiwell plate 400 may help prevent evaporation or contamination of a sample or media disposed in wells 110. The cover 420 may also be configured to fit over the cartridge 110 thereby to reduce possible contamination, to maintain the content of the gas in the wells, or reduce evaporation of fluids disposed in the ports 460 of the cartridge 410.

Figure 5:
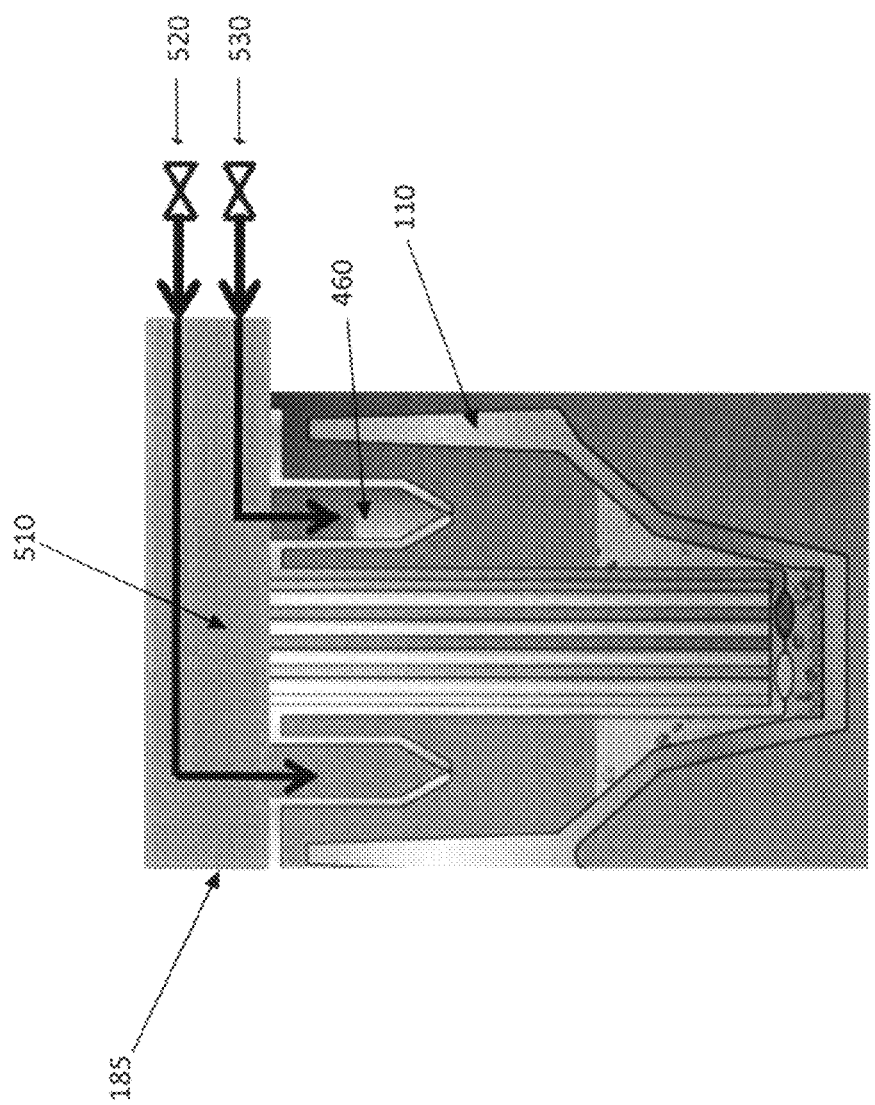
FIG. 5 is a schematic cross sectional view of a well of a well plate including ports disposed thereover for controlling gas content in the well and pneumatically controlling addition of exogenous substances in solution.

FIG. 5 depicts a schematic cross section of a well 110 of an embodiment of the invention showing structure 185 used to add drugs or gasses to wells so as to alter the microenvironment of the samples under examination. Details of the delivery system of the existing, commercially available Seahorse XF Analyzer are described in US 20080014571, the disclosure of which is incorporated herein by reference. The drug delivery manifold 510 may be modified to deliver environmental gases, e.g., an external gas 520, i.e., from a gas cylinder, or internal air 530 to the head space directly above each well. The internal air may be, e.g., ambient air from inside the instrument that is compressed via a small internal compressor, to pressurize the drug ports to deliver drug compounds. The delivery of gas to the head space may allow manipulation of the environment around the test sample to create conditions simulating hypoxia (<5% $O_2$) or normoxia and/or low pH. In some embodiments, a source of oxygen, carbon dioxide, and/or a biologically inert gas may be injected into media in the well or a headspace above the surface of media in the wells for controlling the composition of gas in the headspace or in the media. The gas may be injected into the media or headspace from ports 460.

In particular, one way for achieving this is with the configuration described with respect to FIGS. 2a and 2b, in which a cartridge 410 contains a set of 4 ports 460 that may be used to deliver various compounds to the sample within the wellplate. For example, a common test performed on the XF instrument is a mitochondrial stress test. In this assay a series of injections are delivered through the drug ports of the cartridge in order to measure the response of the biological sample to various compounds (oligomycin, FCCP, rotenone and antimycin). These compounds are preloaded into a drug reservoir (port) on the XF cartridge prior to execution of the assay. When the cartridge is inserted into the instrument it is coupled to a manifold which when activated by a solenoid valve, provides pneumatic pressure to the head space of the reservoir forcing the compound through a small orifice and into the well containing the biological sample. The pneumatic manifold and valve system may be modified to redirect one of these ports to an external gas supply (gas cylinder or bottle). The gas supply may be connected to the instrument through a port on the rear connector panel. The bottle may be located near the instrument and may contain a regulator and bubbler for humidification of the incoming gas. When activated, a solenoid valve may open, allowing the gas to flow through the manifold/cartridge interface, through the drug port orifice, and into the head space above the biological sample. By oscillating the plunger (probe) vertically, the gas will be mixed with the medium allowing control of the available oxygen to the sample. For example, by perfusing argon into the head space, the available $O_2$ in the medium is displaced and a more hypoxic condition is created around the sample. By turning off the gas and mixing, ambient levels of $O_2$ may be re-established.

In some embodiments, a source of a solution of a biologically active substance may be in fluid communication with media in wells for exposing a sample to the substance To control the operation and timing of the solenoid valve, the instrument software may be modified to facilitate control of the valve/timing and to expose some of the calculation variables used during calibration. For example, to calculate molar concentration of $O_2$ in the medium, the concentration at calibration is preferably known and input into the calculation table. Under some conditions the initial calibration value (F or current ambient concentration) may not be known. In this case, calibration and solution of equation (1) (see example 2 below) may be achieved by injecting sodium sulfite into a set of control wells and calibrating the system based on a known F0 value. To calculate these results, certain coefficients may be made accessible in the software. A separate window may be created in the software to facilitate access to these variables, valve control and calculation of calibration coefficients.

The instrument may be tested using a well characterized cell line (mouse C2C12) to verify proper operation and control of the gas system. A series of tests may be conducted to demonstrate the ability to purge $O_2$ from medium and create a hypoxic microenvironment around the sample. These tests may include:

1. Calibration of the instrument under known and unknown ambient $O_2$ concentrations
2. Verify performance of the gas delivery system and the ability to drive environmental $O_2$ levels to desired value (<5% PPO). This may be verified within the instrument by looking at the $O_2$ level data. The readout from the instrument may provide a view that presents this data.

An alternative to controlling $O_2$ and pH within the sample environment may be to enclose the entire instrument in an environmental chamber and pump down the chamber to the desired levels. This alternative approach may be less desirable, as it may be very costly, take up a lot of lab space, and require long periods of time to achieve the desired levels around the tissue. By the time these $O_2$ levels are achieved the tissue may be dead.

Figure 6:
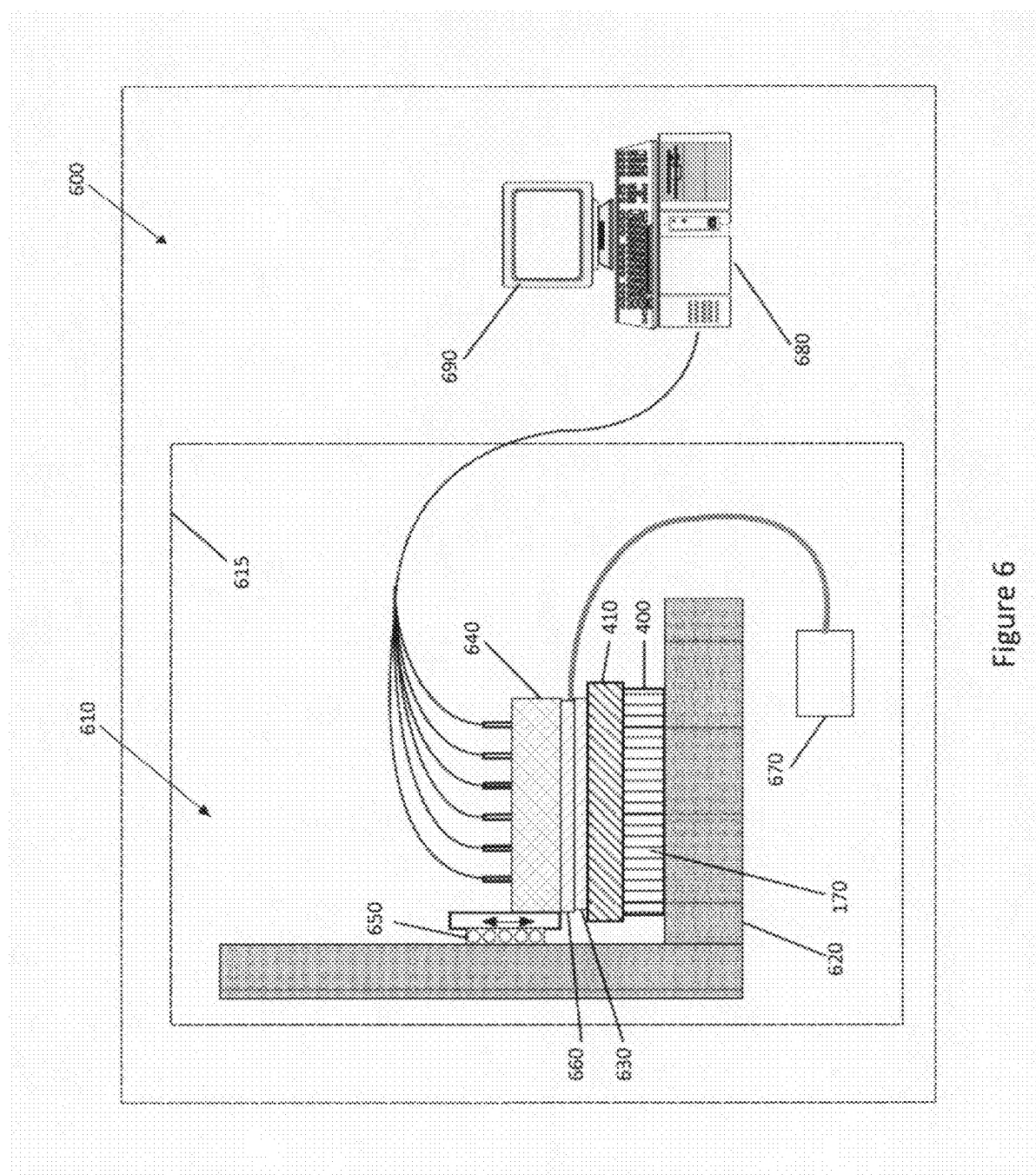
FIG. 6 is a schematic illustration of a measurement system and apparatus in accordance with an embodiment of the invention.

FIG. 6 shows a schematic of an analyzer used in connection with embodiments of the invention. It comprises an apparatus 600 including a compound storage and delivery apparatus 610 disposed in a housing 615 (shown in dashed lines) and includes a cartridge 410 defining a plurality of apertures for receiving sensor structures and a plurality of fluid ports (shown in detail in FIGS. 4a and 4b) compliantly mounted, and a stage or base 130 adapted to receive a multiwell plate 400, e.g., a cell culture plate. The cartridge 410 is disposed above, and adapted to mate with, the multiwell plate 400. The cartridge 410 optionally is held by a cartridge holder 630 adapted to receive the cartridge 410. The apparatus also includes a mounting block 640, which can reciprocate as shown by the double headed arrow, preferably powered by a motor (not shown), including an elevator mechanism 650. The elevator mechanism 650 may be adapted to move the cartridge 410 relative to the stage 620, or well plate 400. The mounting block includes a gas multiplexer 660 attached to a gas supply or gas reservoir 670. The gas supply 670 is in fluid communication with the cartridge, and is used to impel the delivery of test fluid from a port in the cartridge to a well in the multiwell plate 400, or to fix the gas composition in one or more wells. A plurality of probes or plungers 170 with sensors are adapted for insertion into the plurality of apertures in the cartridge 410, and may be used to gather data indicative of the state of cells disposed in wells in the multiwell plate 400.

The compound storage and delivery apparatus 610 is controlled by a controller 680, that may be integrated with a computer 690, that may control the elevator mechanism, the multiplexer, and the pressure source. The controller 680 may, thereby, permit delivery of a test fluid from a port to a corresponding well when an associated sensor is disposed in the well.

The apparatus described herein is a modification of the apparatus disclosed in US 20080014571, referenced above, and enables experimentation with and analysis of three-dimensional cell culture samples, such as a tissue sample, a biopsied sample, or a cell scaffold holding cells. Viability of the sample may be maintained and control exercised over its microenvironment. In certain embodiments, a gas may be added to the media or to a headspace in the well above the media to modify the microenvironment about the sample by altering dissolved gas composition. In certain other embodiments, a solution of a biologically active substance may be added to the media to modify the microenvironment about the sample by exposing the sample to a biologically active substance. A metered amount of one or more gases and/or one or more drugs or other solutes may be added to media in the well to set the microenvironment in the medium about the sample to a predetermined point. The microenvironment in the well may be set to a hypoxic condition. The concentration of one or more solutes in media about the sample may be measured. A plurality of measurements, separated in time, of the concentration of one or more solutes in media about the sample may be taken.

In certain other embodiments, the method includes adding an oxygen scavenger such as sodium sulfite to the medium.

A human biopsied tissue sample may be placed on the nesting site, potential therapeutic drugs may be added to the media, and the effect of the drugs on the sample may be assessed.

EXAMPLES

The following examples illustrate certain exemplary and preferred embodiments and applications of the instant invention, but are not intended to be illustrative of all embodiments and applications.

Example 1

Development of a Custom Injection Molded Wellplate and Perfusion Insert Designed for Tissue Perfusion and Immobilization The Seahorse XF96 flux analyzer was developed and optimized to measure bio-energetic activity in cell based assays. XF measurements are based on a patented method in which a small, temporary measurement volume is created around a monolayer of cells which are adherent to the bottom of the wellplate. A small volume is created when the plunger (probe) is lowered to the bottom of the well (3.8 mm diameter) and engages a set of standoffs (0.20 mm height) to create a volume of approximately 2.25 microliters. The present design of the wellplate is not optimal for use with tissue samples because: (1) samples need to be immobilized and orientated to prevent them from shifting between measurements, (2) lack of a consistent and homogeneous supply of nutrients (perfusion) of the three-dimensional samples, and (3) a larger measurement chamber is required that will accommodate samples up to 200 micrometers thick. In order to adapt the geometry of the wells for use with tissue samples, disclosed herein is a disposable 96-well plate and plunger (probe) system to work within the Seahorse XF96 instrument that immobilizes, orientates, and provides perfusion of tissue samples.

The custom wellplate and perfusion inserts described above are suitable for use with tissue samples. As discussed above, the wellplate may be designed to a standard "Society for Biological Screening" SBS footprint having a 6 mm well diameter with a depression at the bottom of the well 0.5 mm deep, 3 mm diameter, used to orient and control the positioning of samples in the depression at the bottom of the well. The perfusion inserts are designed to slide into the well, with a slight interference to the wall so that the insert is held in place over the sample, and to immobilized the sample in the depression at the bottom of the well.

Example 2

Determining pH and Oxygen Sensor Calibration Coefficients

A wellplate, inserts, and plungers (probes) may be assembled and installed in a specialized heatsink that provides alignment and thermal control of the samples. Appropriate position offsets and a calibration protocol for the sensors may be developed. The calibration protocol consists of determining the appropriate volumes, diffusion constants, and sensor gains that are unique to the plate, insert, and probe geometry. These constants may be calculated using calibration reagents titrated to known concentrations to develop a set of coefficients that describe the signal outputs as a function of analyte concentration ($O_2$ or $H^-$). For example; when calibrating the pH sensor the optical signals (based on a 16 bit readout) are normalized to a starting $H^-$ concentration (pH 7.4) by determining the excitation intensity for each probe that provides a desired starting signal at pH 7.4. The signal at different $H^+$ concentration is recorded to develop a standard curve. The coefficients for the standard curve are then loaded into the instrument so that each sensor is calibrated over a range of concentrations to be measured. A similar calibration for the Oxygen sensor may be performed by normalizing the outputs under ambient $O_2$ concentrations (PPO=155 mm Hg), and determining a second calibration point by injecting sodium sulfite (an oxygen scavenger) to generate a calibration point at zero (PPO=0 mm Hg). The Stern Volmer quenching constant may be calculated based on equation 1 below and this relationship used to calculate the $O_2$ level at each time point during the experiment.

$$K=1/O_2(F_0/F-1) \quad \text{(equation 1)}$$

Where
K=Stern Volmer constant
$F_0$=signal output at zero $O_2$
F=signal output at ambient
$O_2$=concentration of $O_2$ at ambient Example 3

Validation and Selection of Best Insert Geometry

Once the calibration coefficients are established and uploaded to the instrument a series of tests may be conducted to determine the best geometry for the perfusion inserts. These tests may involve taking repeated OCR/ECAR measurements of a standard, well characterized cell line such as C2C12 fibroblasts. After each measurement the plungers (probes) may be oscillated to perfuse the measurement chamber and optimize the timing, Z travel, and speed to get the best perfusion. The best perfusion may be determined based on the ability of the system to restore the measurement chamber to the starting concentration of $O_2$ and pH.

Examples 4-6

Experimental Studies Using Embodiments of the Invention

A prototype device was fabricated to evaluate various geometric properties and applications of embodiments of the invention, as discussed below in examples 4-6. The device includes a plurality of cylindrical vessels fitted with a polycarbonate perfusion insert. The insert is fitted to the bottom of the vessel to form a pair of chambers within the vessel that are connected through a 1.5 mm port. The upper chamber consists of a reservoir of media which is approximately 30 times the volume of the lower chamber. The inside diameter of the insert engages the Seahorse sensor cartridge to form a piston-like pump having a stroke length of approximately 5 mm and a diameter of 3 mm. The plunger of the Seahorse sensor cartridge, when moved through the inner diameter of the insert, forces media from the upper section of the chamber, through the port, into the lower chamber from which it exits through a set of peripheral vents between the inside diameter of the vessel and the outside diameter of the insert. With each stroke of the cartridge, a volume of fluid is perfused through the lower chamber such that the fluid turnover is a minimum of 2 times the static volume. At the bottom of the lower chamber is disposed a depression in the vessel (1 mm×0.25 mm) where, during use, a spherical micro-tissue is positioned for measurement. During a measurement, the cartridge comes to rest on a surface where the sensors are positioned in the center of the port which isolates the top chamber from the bottom chamber. The sensors are thus positioned over the micro-tissue, sealing the lower chamber from the upper chamber. Within this reduced volume of fluid, measurements are collected from the sensors to record the oxygen and pH concentrations at various timed intervals. From this data the oxygen and pH flux (dO/dT), (dpH/dT) are determined. This method has been used to evaluate the geometric properties of the insert to optimize fluid turnover while maintaining tissue position and to facilitate measurements of the metabolic properties of the tissues.

Example 4

Figure 7:
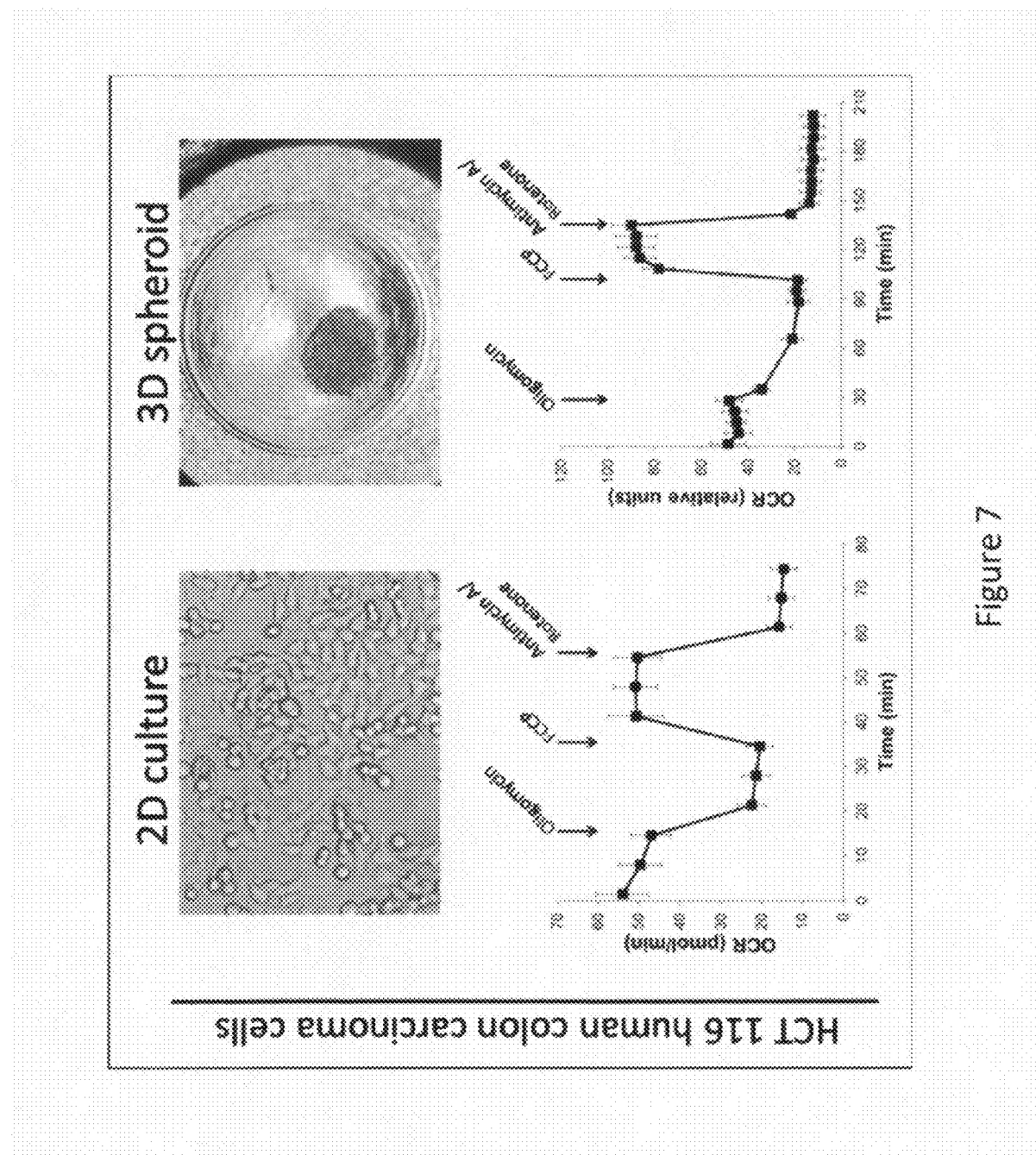
FIG. 7 includes graphs and micrographs illustrating mitochondiral Stress Test results comparing 2D and 3D cultures of HCT116 cells.

Feasibility for measuring single 3D spheroids using prototype inserts and plates has been demonstrated. For example, referring to FIG. 7, colon carcinoma cells (HTC116) grown in 2D mono-layer culture are compared to cells formed in a 3D Spheroid (using the hanging drop method) using a Seahorse Bioscience Mitochondrial Stress Test (MST). The spheroid image on the right shows a single micro-tissue sitting in the 1 mm×0.25 mm relief in the bottom of the well (size approximately 200 microns). The signatures reveal distinct differences in the spare respiratory capacity between the two culture types (maximum respiration, basal). A possible theoretical explanation is that the cells grown in 2D are highly proliferative and thus use a higher fraction of the basal OCR to support growth, whereas cells in 3D (n=3) have two fold higher spare capacities. The 3D cultures, in this example, also exhibit distinct differences in the kinetic response to drug exposure (oligomycin injection) as demonstrated by the slower response in the 3D cultured spheroids.

Example 5

Figure 8:
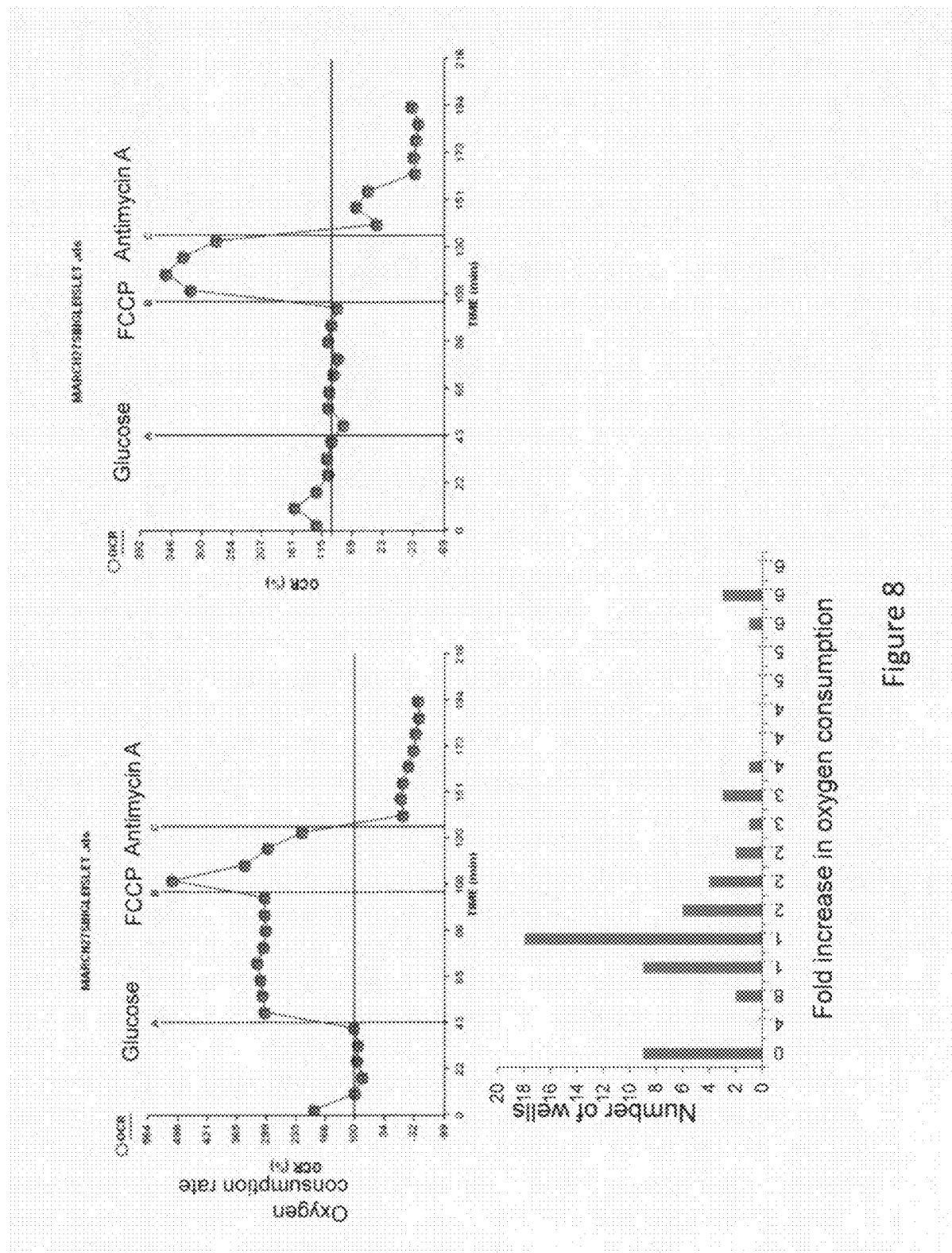
FIG. 8 includes graphs illustrating glucose response for single pancreatic islets measured in a prototype perfusion plate in accordance with an embodiment of the invention.

The ability to perfuse, maintain and measure metabolic profiles of single islets using a prototype chamber has been demonstrated. For example, referring to FIG. 8, single pancreatic islets (approximately 100 microns diameter) are inserted into the plates (1 per well) and exposed to serial injections of 15 mM glucose, introducing FCCP and Antimycin A. These signatures reveal the ability to measure discrete changes respiration in response to a 15 mM injection of glucose. Further, by measuring single islets (1 per well) one can directly compare and interrogate differences in the metabolic signatures between islet populations to determine function. For example, islets in the chart on the upper left respond to glucose whereas islets in the upper right do not. These measurements facilitate binning into groups, dependent on fold increase in oxygen consumption in response to glucose, allowing islets to be ranked for quality control prior to transplantation. In future work, this data may be correlated to a set of glucagon and insulin biomarkers co-located in the in the perfusion path using an in situ ELISA assay to correlate oxygen consumption to insulin and glucagon secretion.

Example 6

Figure 9:
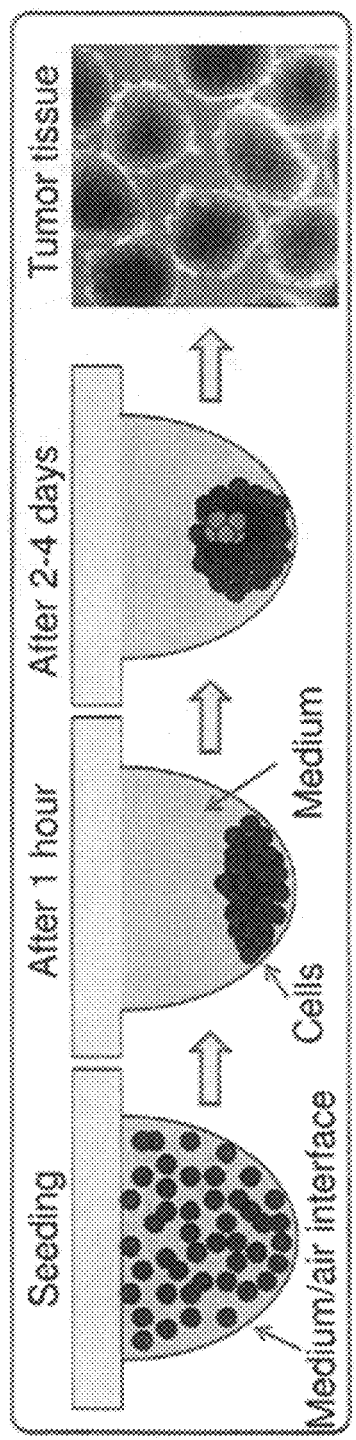
FIG. 9 includes schematic cross sectional views and a top view of a well in which cells are allowed to coalesce in accordance with an embodiment of the invention.
Figure 9:
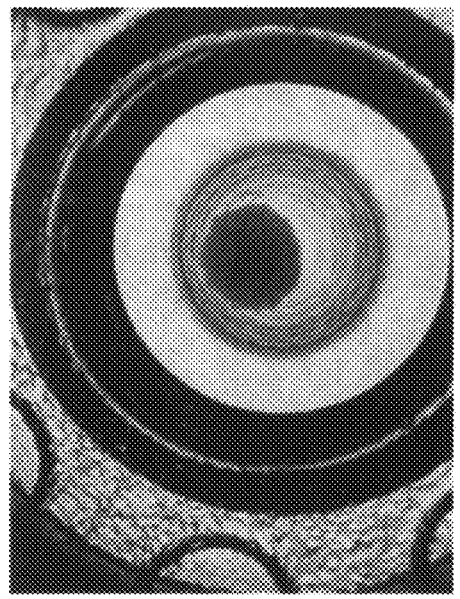
Figure 10:
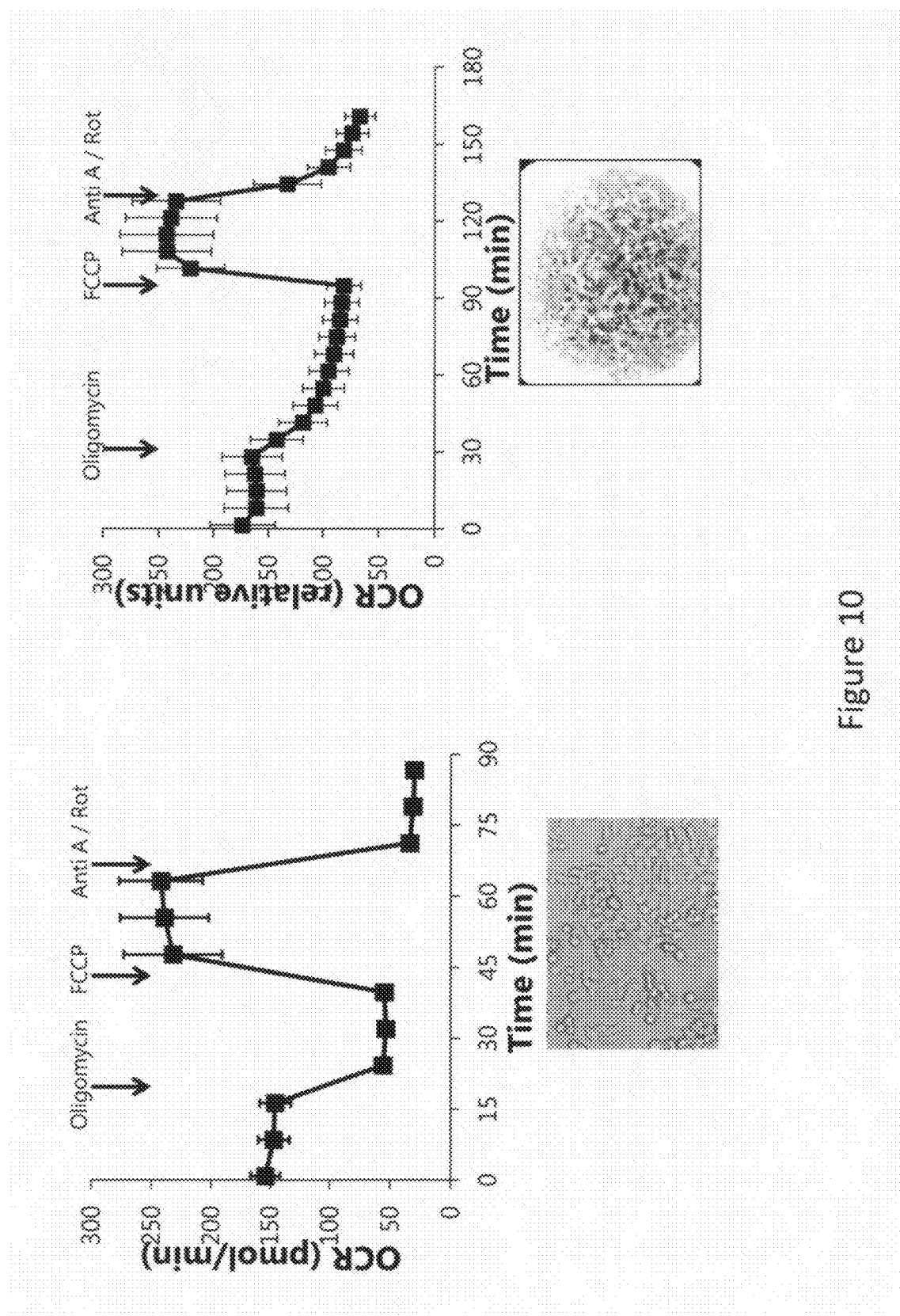
FIG. 10 includes graphs and micrographs illustrating the generation of scaffolded discs.

3D micro-tissues ranging in size from 50-600 microns have been generated. For example, using the hanging drop method, cells are seeded with 40 μl of media into a commercially available seeding lid provided by InSphero Bioscience (Zurich, Switzerland). Referring to FIG. 9, cells with media are allowed to coalesce in the bottom of the droplet, where after 4 days they form a unified sphere containing cells and self-generated extra cellular matrices (ECMs, i.e., material that surrounds/coats cells as they form tissue, generally consisting of protein matrices that define the micro-environment around the cell). Once the spheroids are formed they are placed into storage plate with an additional 100 μl of media where they are maintained until ready to use. Using this method, 3D spheroids have been generated from Hep G2's (human liver carcinoma) and HCT 116 (human colorectal carcinoma). These cell lines have been shown to form uniform sized spheroids both as mono-cultures and co-cultures. In addition, referring to FIG. 10, scaffolded discs containing MCF-7 (breast ductal carcinoma) have been successfully generated. These scaffolds were created using 2 mm diameter cellulosic filter paper (whatman 114), placed into the bottom of a Seahorse perfusion micro-chamber and measured for bioenergetics function using the Seahorse MST protocol. This demonstrates that it is feasible to assemble, maintain, and measure bio-energetic function of both self-assembling spheroids and scaffold micro-discs.

Figure 11:
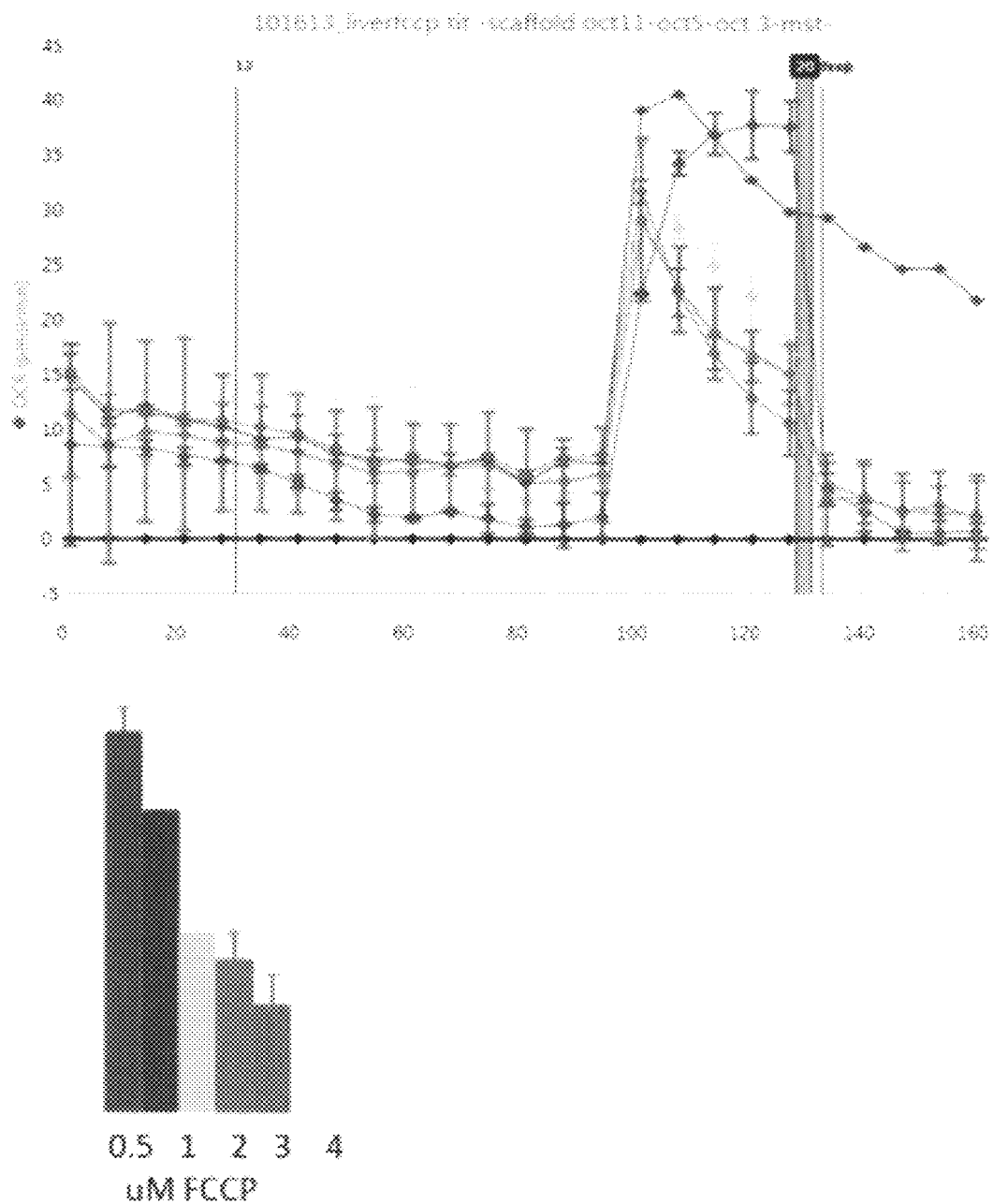
FIG. 11 is a graph illustrating measured respiratory capacity of liver micro-tissue, as function of carbonylcyanide-p-trifluoromethoxyphenylhydrazone (FCCP) concentration.

Referring to FIG. 11, spheroids may be used to perform a test for mitochondrial toxicity. In this example hepatocytes are co-cultured with non-parenchymal (Kupffer cell, etc.) cells to form a liver micro-tissue that presents a functional immune response. The system is used to screen the tissues for toxicity by introducing FCCP and measuring respiratory capacity (FCCP stimulated vs basal OCR). This test demonstrates that the assay may be optimized for measuring mitochondrial function by first finding the optimum concentration of FCCP that gives the maximum difference between stimulated and unstimulated OCR.

The invention may be embodied in other specific forms without departing from the spirit or essential characteristics thereof. The foregoing embodiments are therefore to be considered in all respects illustrative of the invention described herein. Various features and elements of the different embodiments can be used in different combinations and permutations, as will be apparent to those skilled in the art. Scope of the invention is thus indicated by the appended claims rather than by the foregoing description, and all changes which come within the meaning and range of equivalency of the claims are therefore intended to be embraced herein.

What is claimed is:

1. An apparatus for conducting analysis of a three-dimensional cell sample, the apparatus comprising:
a plurality of wells for holding respective samples and sample media, at least one of the wells comprising
a sample nesting site disposed in a bottom surface of the well,
disposed thereabove a bore dimensioned to interfit with a plunger which moves vertically down within and relative to the bore and within the sample media disposed in the well, and
a media channel defined by the well, a removable well insert, or both the well and the insert, in fluid communication with the sample nesting site, which permits flow of the sample media therethrough impelled by the plunger and permits exposure of the sample to flowing media as the plunger moves.

2. The apparatus of claim 1 wherein the plunger moves relative to the nesting site to induce perfusion of media about the sample.

3. The apparatus of claim 1 wherein said media channel comprises a fluid path which returns media perfused about the sample back to media disposed in the well.

4. The apparatus of claim 1 wherein at least said bore is defined by the removable well insert.

5. The apparatus of claim 1 wherein the well comprises a sump in fluid communication with the media channel.

6. The apparatus of claim 1 wherein said sample nesting site is disposed within a sump for collection of media and in fluid communication with said media channel.

7. The apparatus of claim 1 wherein said media channel comprises a fluid path defining a closed loop beneath the surface of media in the wells to permit media perfusive flow about said sample on both upward and downward movement of a plunger within said bore.

8. The apparatus of claim 1 further comprising a sensor for detecting the concentration of a solute in media disposed about said sample.

9. The apparatus of claim 1 comprising a plurality of plungers adapted for reciprocating movement within the bores of respective wells.

10. The apparatus of claim 1 wherein the plurality of wells defines a multiwell plate comprising 24 or 96 wells.

11. The apparatus of claim 1 further comprising a source of oxygen, carbon dioxide, and/or a biologically inert gas in fluid communication with media in a well or a headspace above the surface of media in the wells for controlling the composition of gas in the headspace or in the media.

12. The apparatus of claim 1 further comprising a source of a solution of a biologically active substance in fluid communication with media in wells for exposing a sample to said substance.

13. The apparatus of claim 1 further comprising a three-dimensional cell growth scaffold disposed on said sample nesting site.

14. The apparatus of claim 1 further comprising a check valve disposed in said media channel to inhibit media perfusion from the channel back to the sample.

15. An apparatus for conducting analysis of three-dimensional cell samples, the apparatus comprising:
  a well for holding a sample and sample media comprising
    a sample nesting site disposed in a bottom surface of the well,
    disposed above said nesting site, a bore dimensioned to interfit with a plunger which moves vertically down within the bore and within media disposed in said well,
    a media channel in fluid communication with said sample nesting site which permits media perfusion about said sample, wherein the media channel is defined by the well, a removable well insert, or both the well and the insert, and
  a plunger adapted for reciprocal movement in said bore thereby to impel media perfusion about said sample,
  wherein the media channel permits flow of the sample media disposed in the well therethrough impelled by the plunger and permits exposure of the sample to flowing media as the plunger moves.

16. The apparatus of claim 15 further comprising a sensor for detecting the concentration of a dissolved media component in media about the sample nesting site.

17. A method of impelling media flow about a three-dimensional cell culture sample, so as to maintain viability of the sample and exercise control over its microenvironment, the method comprising the steps of:
  providing a well including a sample nesting site disposed in a bottom surface of the well, a bore dimensioned to interfit with a plunger disposed above the sample nesting site, a media channel in fluid communication with said sample nesting site, wherein the media channel is defined by the well, a removable well insert, or both the well and the insert, and a plunger adapted for reciprocal movement in said bore;
  placing a sample on the sample nesting site in medium within the well, and
  moving said plunger within the bore to impel media flow about the sample and through said channel thereby to perfuse the sample with media,
  wherein the media channel permits flow of the sample media disposed in the well therethrough impelled by the plunger and permits exposure of the sample to flowing media as the plunger moves.

18. The method of claim 17 comprising the additional step of adding a gas to the media or to headspace in the well above the media to modify the microenvironment about the sample by altering dissolved gas composition.

19. The method of claim 17 comprising the additional step of adding a solution of a biologically active substance to the media to modify the microenvironment about the sample by exposing the sample to the biologically active substance.

20. The method of claim 17 comprising the additional step of measuring the concentration of one or more solutes in media about said sample.

21. The method of claim 17 comprising the additional step of making a plurality of measurements separated in time of the concentration of one or more solutes in media about said sample.

22. The method of claim 17 comprising the additional step of adding at least one of a metered amount of one or more gases and one or more solutes to media in said well thereby to set the microenvironment in the medium about said sample to a predetermined point.

23. The method of claim 17 wherein the sample is a tumor sample, the method comprising the additional step of adding a metered amount of one or more gases and/or one or more solutes to media in said well thereby to set the microenvironment in the medium about said sample to a predetermined point simulating the microenvironment of the tumor sample in vivo.

24. The method of claim 17 comprising multiplexing said method by the steps of:
  providing a plurality of said wells including sample nesting sites, bores dimensioned to interfit with plungers disposed above the sample nesting sites, media channels in fluid communication with said sample nesting site, and plungers adapted for reciprocal movement in said bore;
  placing a sample on the sample nesting sites in media within the plurality of wells,
  moving the plurality of said plungers within the bores to impel media flow about the samples and through said channels thereby to perfuse the samples with media, and
  measuring one or more times the concentration of one or more solutes in media about said samples in the plurality of said wells.

25. The method of claim 17 comprising the additional step of placing one or a plurality of beads bearing immobilized binders for biomolecules of interest secreted from or absorbed by the sample in the media and using the beads to detect the presence or concentration of said biomolecules in the microenvironment of the sample.

* * * * *